(12) United States Patent
Kragh et al.

(10) Patent No.: US 7,166,453 B2
(45) Date of Patent: Jan. 23, 2007

(54) POLYPEPTIDE

(75) Inventors: Karsten Matthias Kragh, Viby (DK); Harm Mulder, Copenhagen (DK); Steffen Petersen, Aalborg (DK); Helle Fomsgaard, Aalborg (DK); Oene Robert Veltman, Aalborg (DK)

(73) Assignee: Danisco A/S, Copenhagen (DK)

( * ) Notice: Subject to any disclaimer, the term of this patent is extended or adjusted under 35 U.S.C. 154(b) by 49 days.

(21) Appl. No.: 10/864,874

(22) Filed: Jun. 10, 2004

(65) Prior Publication Data

US 2005/0037391 A1 Feb. 17, 2005

Related U.S. Application Data

(60) Provisional application No. 60/479,505, filed on Jun. 19, 2003.

(30) Foreign Application Priority Data

Jun. 13, 2003 (GB) ................. 0313754.4

(51) Int. Cl.
*C12N 9/28* (2006.01)
*C12N 15/00* (2006.01)
*C12N 9/88* (2006.01)
*C07H 21/04* (2006.01)

(52) U.S. Cl. ............... 435/202; 435/69.1; 435/200; 435/201; 435/183; 536/23.74

(58) Field of Classification Search ........... 435/183, 435/202, 69.1
See application file for complete search history.

(56) References Cited

U.S. PATENT DOCUMENTS 6,667,065 B1 12/2003 Kragh et al. ............ 426/28

FOREIGN PATENT DOCUMENTS

| EP | 0 298 645 A2 | 11/1989 |
|----|---|---|
| EP | 0 494 233 | 4/1991 |
| WO | WO 99/50399 | 10/1999 |
| WO | WO 02/068589 A2 | 9/2002 |

OTHER PUBLICATIONS

Christophersen et al., "Enzymatic Characterisation of Novamyl®, a Thermostable α-Amylase," Starch Starke, Wiley-VCH Verlag, DE, vol. 50, No. 1, 1998, pp. 39-45.
Zhou, J. et al, "Nucleotide sequence of the maltotetraohydrolase gene from *Pseudomonas saccharophila*," FEBS Letters, vol. 255, 1989, pp. 37-41.
Fogarty, W., 1983, Microbial Amylases, W.M. Fogarty (Ed.) Microbial enzymes and biotechnology, Applied Sicence, London, pp. 1-92.
Fogarty, W. et al, "Starch-Degrading Enzymes of Microbial Origin," M.J. Bull (Ed.), Progress in Industrial Microbiology, vol. 15, Elsevier Scientific, 1979, pp. 87-150.
Kainuma, K. et al, "Isolation and action pattern of maltohexaose producing amylase from *aerobacter aerogenes*," FEBS Letters, vol. 26, No. 1, Oct. 1972, pp. 281-285.

*Primary Examiner*—Rebecca E. Prouty
*Assistant Examiner*—Mohammad Meah
(74) *Attorney, Agent, or Firm*—Steptoe & Johnson LLP

(57) ABSTRACT

We disclose a PS4 variant polypeptide derivable from a parent polypeptide, the parent polypeptide having non-maltogenic exoamylase activity, which PS4 variant polypeptide comprises one or more of the following substitutions: G69P, A141P, G223A, A268P, G313P, S399P and G400P, with reference to the position numbering of a *Pseudomonas saccharophilia* exoamylase sequence shown as SEQ ID NO: 1. Such PS4 variant polypeptides may be used as exoamylases, particularly as non-maltogenic exoamylases. Combinations of such PS4 variant polypeptides together with Novamyl are disclosed.

24 Claims, 3 Drawing Sheets

POLYPEPTIDE

The present application claims priority under 35 U.S.C. § 119(e) to U.S. Provisional Application No. 60/479,505, filed Jun. 19, 2003, and under 35 U.S.C. § 119(a) to United Kingdom Application No. GB 0313754.4, filed Jun. 13, 2003, each of which is expressly incorporated by reference herein in its entirety.

FIELD

This invention relates to polypeptides, and nucleic acids encoding these, and their uses as non-maltogenic exoamylases in producing food products. In particular, the polypeptides are derived from polypeptides having non-maltogenic exoamylase activity, in particular, glucan 1,4-alpha-maltotetrahydrolase (EC 3.2.1.60) activity.

SUMMARY

According to a first aspect of the present invention, we provide a PS4 variant polypeptide derivable from a parent polypeptide, the parent polypeptide having non-maltogenic exoamylase activity, which PS4 variant polypeptide comprises one or more of the following substitutions: G69P, A141P, G223A, A268P, G313P, S399P and G400P, with reference to the position numbering of a *Pseudomonas saccharophilia* exoamylase sequence shown as SEQ ID NO: 1.

Preferably, the parent polypeptide comprises a non-maltogenic exoamylase. Preferably, the parent polypeptide comprises a glucan 1,4-alpha-maltotetrahydrolase (EC 3.2.1.60). Preferably, the parent polypeptide is or is derivable from *Pseudomonas* species, preferably *Pseudomonas saccharophilia* or *Pseudomonas stutzeri*. Preferably, the parent polypeptide is a non-maltogenic exoamylase from *Pseudomonas saccharophilia* having a sequence shown as SEQ ID NO: 1. Alternatively, or in addition, the parent polypeptide is a non-maltogenic exoamylase from *Pseudomonas stutzeri* having SWISS-PROT accession number P13507.

In preferred embodiments, the PS4 variant polypeptide has a higher thermostability compared to the parent polypeptide when tested under the same conditions. Preferably, the half life ($t_{1/2}$), preferably at 60 degrees C., is increased by 15% or more, preferably 50% or more, most preferably 100% or more, relative to the parent polypeptide. Preferably, the PS4 variant polypeptide has a higher pH stability compared to the parent polypeptide when tested under the same conditions. Preferably, the PS4 variant polypeptide has 10% or more, preferably 20% or more, preferably 50% or more, pH stability.

In preferred embodiments, the PS4 variant polypeptide comprises one or more proline substitutions selected from the group consisting of: G69P, A141P, A268P, G313P, S399P and G400P, together with an alanine substitution G223A.

Preferably, it comprises a sequence selected from the group consisting of: PSac-69P (SEQ ID NO: 2), PSac-A141P (SEQ ID NO: 3), PSac-G223A (SEQ ID NO: 4), PSac-A268P (SEQ ID NO: 5), PSac-G313P (SEQ ID NO: 6), PSac-S399P (SEQ ID NO: 7), PSac-G400P (SEQ ID NO: 8), PStu-69P (SEQ ID NO: 12), PStu-A141P (SEQ ID NO: 13), PStu-G223A (SEQ ID NO: 14), PStu-A268P (SEQ ID NO: 15), PStu-G313P (SEQ ID NO: 16), PStu-S399P (SEQ ID NO: 17) and PStu-G400P (SEQ ID NO: 18).

There is provided, according to a second aspect of the present invention, a nucleic acid comprising a sequence capable of encoding a PS4 variant polypeptide according to the first aspect of the invention.

We provide, according to a third aspect of the present invention, a PS4 nucleic acid sequence derivable from a parent sequence encoding a polypeptide having non-maltogenic exoamylase activity and comprising a codon encoding an amino acid at the specified position selected from the group consisting of: 69P, 141P, 223A, 268P, 313P, 399P and 400P, with reference to the position numbering of a *Pseudomonas saccharophilia* exoamylase sequence shown as SEQ ID NO: 1.

As a fourth aspect of the present invention, there is provided a nucleic acid sequence derivable from a parent sequence, the parent sequence capable of encoding a non-maltogenic exoamylase, which nucleic acid sequence comprises a substitution at one or more residues such that the nucleic acid encodes one or more of the following mutations at the positions specified: 69P, 141P, 223A, 268P, 313P, 399P and 400P, with reference to the position numbering of a *Pseudomonas saccharophilia* exoamylase sequence shown as SEQ ID NO: 1.

Preferably, the PS4 nucleic acid sequence is derived from a parent sequence encoding a non-maltogenic exoamylase by substitution of one or more nucleotide residues.

Preferably, it comprises a codon CCA, CCC, CCG or CCT, at any one or more of positions 207–209, 423–425, 804–806, 939–941, 1197–1199, 1200–1202, and/or a codon GCA, GCC, GCG or GCT at positions 669–671, with reference to the position numbering of a *Pseudomonas saccharophilia* exoamylase nucleotide sequence shown as SEQ ID NO: 10. Preferably, the parent sequence encodes a non-maltogenic exoamylase having a feature as set out above, or in which a polypeptide encoded by the nucleic acid has any of the features as set out above.

We provide, according to a fifth aspect of the present invention, a plasmid comprising a PS4 nucleic acid according to the second, third or fourth aspect of the invention.

The present invention, in a sixth aspect, provides an expression vector comprising a PS4 nucleic acid to the second, third or fourth aspect of the invention, or capable of expressing a PS4 variant polypeptide according to the first aspect of the invention.

In a seventh aspect of the present invention, there is provided a host cell comprising, preferably transformed with, a plasmid according to the fifth aspect of the invention or an expression vector according to the sixth aspect of the invention.

According to an eighth aspect of the present invention, we provide a cell capable of expressing a polypeptide according to the first aspect of the invention.

Preferably, the cell or host cell is a bacterial, fungal or yeast cell.

We provide, according to a ninth aspect of the invention, a method of expressing a PS4 variant polypeptide, the method comprising obtaining a host cell according to the seventh aspect of the invention, or a cell according to the eighth aspect of the invention, and expressing the polypeptide from the cell or host cell, and optionally purifying the polypeptide.

There is provided, in accordance with a tenth aspect of the present invention, a method of altering the sequence of a polypeptide by introducing an amino acid substitution selected from the group consisting of: G69P, A141P, G223A, A268P, G313P, S399P and G400P (with reference to the position numbering of a *Pseudomonas saccharophilia* exoamylase sequence shown as SEQ ID NO: 1), into a parent polypeptide having non-maltogenic exoamylase activity.

As an eleventh aspect of the invention, we provide a method of altering the sequence of a non-maltogenic exoamylase by introducing a G69P, A141P, G223A, A268P, G313P, S399P or G400P substitution, with reference to the position numbering of a *Pseudomonas saccharophilia* exoamylase sequence shown as SEQ ID NO: 1.

Preferably, the sequence of the non-maltogenic exoamylase is altered by altering the sequence of a nucleic acid which encodes the non-maltogenic exoamylase.

In highly preferred embodiments, the non-maltogenic exoamylase has a feature as set out above, or in which a polypeptide encoded by the nucleic acid has a feature as set out above.

We provide, according to a twelfth aspect of the invention, a method of producing a PS4 polypeptide variant, the method comprising introducing an amino acid substitution into a parent polypeptide having non-maltogenic exoamylase activity, the amino acid substitution being selected from the group consisting of: G69P, A141P, G223A, A268P, G313P, S399P and G400P, with reference to the position numbering of a *Pseudomonas saccharophilia* exoamylase sequence shown as SEQ ID NO: 1.

Preferably, the sequence of a nucleic acid encoding the parent polypeptide is altered to introduce the amino acid substitution. Preferably, the parent sequence encodes a non-maltogenic exoamylase, preferably having a feature as set out above, or in which a polypeptide encoded by the nucleic acid has a feature as set out above.

According to a thirteenth aspect of the present invention, we provide a method of altering the sequence of a nucleic acid encoding a non-maltogenic exoamylase, the method comprising introducing into the sequence a codon which encodes an amino acid residue selected from the group consisting of: 69P, 141P, 223A, 268P, 313P, 399P or 400P, with reference to the position numbering of a *Pseudomonas saccharophilia* exoamylase sequence shown as SEQ ID NO: 1.

There is provided, according to a fourteenth aspect of the present invention, a method of increasing the thermostability, or the pH stability, or both, of a polypeptide, the method comprising the steps as set out above.

Preferably, the polypeptide is isolated or purified, or both.

We provide, according to a fifteenth aspect of the present invention, a polypeptide obtainable by a method according to any of the ninth to fourteenth aspects of the invention.

According to a sixteenth aspect of the present invention, we provide a polypeptide obtained by a method according to any of the ninth to fourteenth aspects of the invention.

According to a seventeenth aspect of the present invention, we provide use of a PS4 variant polypeptide according to the first, sixteenth or seventeenth aspect of the invention, as an amylase.

We provide, according to an eighteenth aspect of the present invention, a process for treating a starch comprising contacting the starch with a polypeptide according to any of the first, sixteenth and seventeenth aspects of the invention, and allowing the polypeptide to generate from the starch one or more linear products.

According to a nineteenth aspect of the present invention, we provide use of a PS4 variant polypeptide according to any of the first, sixteenth and seventeenth aspects of the invention, a nucleic acid according to the second, third, fourth or fifth aspect of the invention, a cell or a host cell according to the seventh or eighth aspect of the invention, in preparing a food product.

As an twentieth aspect of the invention, we provide a process of preparing a food product comprising admixing a polypeptide according to any of the first, sixteenth and seventeenth aspects of the invention with a food ingredient.

In preferred embodiments, the food product is a dough product. Examples include in general any processed dough product, including fried, deep fried, roasted, baked, steamed and boiled doughs, such as steamed bread and rice cakes. In highly preferred embodiments, the food product is a bakery product.

According to an twenty-first aspect of the present invention, we provide a process for making a bakery product comprising: (a) providing a starch medium; (b) adding to the starch medium a PS4 variant polypeptide according to any of the first, sixteenth and seventeenth aspects of the invention; and (c) applying heat to the starch medium during or after step (b) to produce a bakery product.

In preferred embodiments, the bakery product is a bread.

According to a twenty-second aspect of the present invention, we provide a food product or a bakery product obtained by a process according to any of the nineteenth to twenty-first aspects of the invention.

Preferably, the food product is a dough or an animal feed.

According to a twenty-third aspect of the present invention, we provide an improver composition for a dough, in which the improver composition comprises a PS4 variant polypeptide according to any of the first, sixteenth and seventeenth aspects of the invention and at least one further dough ingredient or dough additive.

According to a twenty-fourth aspect of the present invention, we provide composition comprising a flour and a PS4 variant polypeptide according to any of the first, sixteenth and seventeenth aspects of the invention.

According to a twenty-fifth aspect of the present invention, we provide use of a PS4 variant polypeptide according to any of the first, sixteenth and seventeenth aspects of the invention, in a bread product to retard or reduce detrimental staling, preferably starch retrogradation, of the bread product.

According to a twenty-sixth aspect of the present invention, we provide an enzyme variant derivable from a parent enzyme, which parent enzyme is a member of the PS4 exoamylase family, in which the enzyme variant comprises one or more amino acid modifications at one or more of the following positions (using *Pseudomonas saccharophilia* exoamylase X16732 numbering) relative to the parent enzyme: G69P, A141P, G223A, A268P, G313P, S399P and G400P or equivalent position(s) in other homologous members of the PS4 exoamylase family.

According to a twenty-seventh aspect of the present invention, we provide a polypeptide being a variant of an exoamylase, which polypeptide comprises a sequence of an exoamylase together with a proline substitution at or about an amino acid position corresponding to position 69, 141, 268, 313, 399 or 400, or an alanine substitution at position 223, or both, of a *Pseudomonas saccharophilia* exoamylase sequence shown as SEQ ID NO: 1.

According to a twenty-eighth aspect of the present invention, we provide a polypeptide sequence comprising a sequence of a non-maltogenic exoamylase which has been mutated to include a proline substitution at an amino acid position 69, 141, 268, 313, 399 or 400 or an alanine substitution at position 223, or both.

According to a twenty-ninth aspect of the present invention, we provide a nucleic acid sequence derivable from a parent sequence encoding a polypeptide having non-maltogenic exoamylase activity and comprising a codon capable of encoding an amino acid substitution selected from the group consisting of: G69P, A141P, G223A, A268P, G313P, S399P and G400P, with reference to the position numbering of a *Pseudomonas saccharophilia* exoamylase sequence shown as SEQ ID NO: 1.

Sequence Listings

Figure 1:
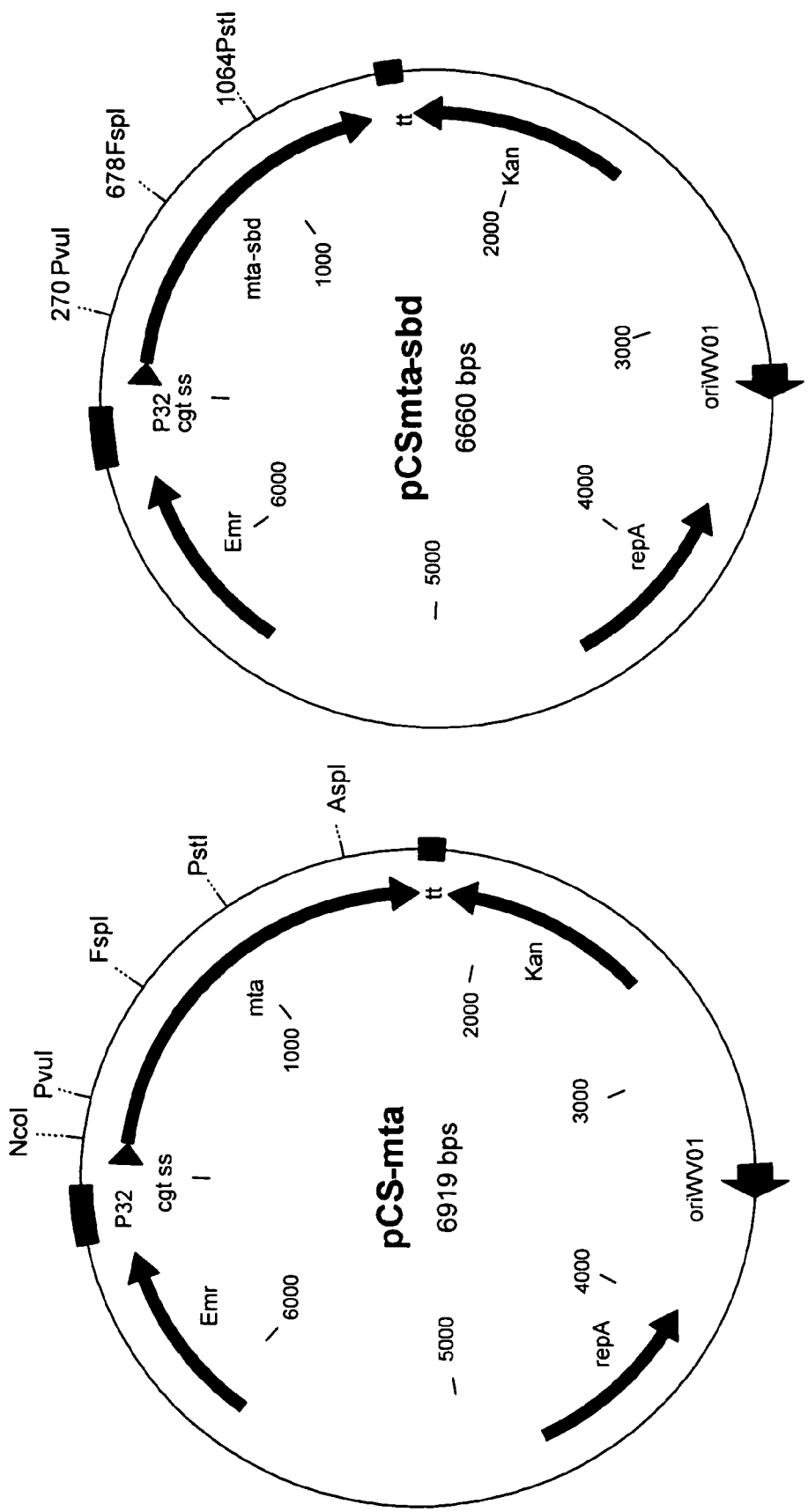
FIG. 1. The *E. coli Bacillus* shuttle vectors pCSmta and pCSmta-SBD with the mta gene under control of the P32 promoter and the cgt signal sequence for extracellular expression of PS4 in *B. subtilis*.

SEQ ID NO: 1 shows a PS4 reference sequence, derived from *Pseudomonas saccharophila* maltotetrahydrolase amino acid sequence.

SEQ ID NO: 2 shows the sequence of PSac-G69P; *Pseudomonas saccharophila* maltotetrahydrolase amino acid sequence with P substitution for G residue at position 69. SEQ ID NO: 3 shows the sequence of PSac-A141P; *Pseudomonas saccharophila* maltotetrahydrolase amino acid sequence with P substitution for A residue at position 141. SEQ ID NO: 4 shows the sequence of PSac-G223A; *Pseudomonas saccharophila* maltotetrahydrolase amino acid sequence with A substitution for G residue at position 223

SEQ ID NO: 5 shows the sequence of PSac-A268P; *Pseudomonas saccharophila* maltotetrahydrolase amino acid sequence with P substitution for A residue at position 268. SEQ ID NO: 6 shows the sequence of PSac-G313P; *Pseudomonas saccharophila* maltotetrahydrolase amino acid sequence with P substitution for G residue at position 313. SEQ ID NO: 7 shows the sequence of PSac-S399P; *Pseudomonas saccharophila* maltotetrahydrolase amino acid sequence with P substitution for S residue at position 399. SEQ ID NO: 8 shows the sequence of PSac-G400P; *Pseudomonas saccharophila* maltotetrahydrolase amino acid sequence with P substitution for G residue at position 400.

SEQ ID NO: 9 shows an amino acid sequence of *Pseudomonas saccharophila* maltotetrahydrolase. *Pseudomonas saccharophila* Glucan 1,4-alpha-maltotetrahydrolase precursor (EC 3.2.1.60) (G4-amylase) (Maltotetraose-forming amylase) (Exo-maltotetraohydrolase) (Maltotetraose-forming exo-amylase). SWISS-PROT accession number P22963.

SEQ ID NO: 10 shows a nucleic acid sequence of *Pseudomonas saccharophila* maltotetrahydrolase. *P. saccharophila* mta gene encoding maltotetraohydrolase (EC number=3.2.1.60). GenBank accession number X16732.

SEQ ID NO: 11 shows an amino acid sequence of *Pseudomonas stutzeri* maltotetrahydrolase.

SEQ ID NO: 12 shows the sequence of PStu-69P; *Pseudomonas stutzeri* maltotetrahydrolase amino acid sequence with P substitution for G residue at position 69. SEQ ID NO: 13 shows the sequence of PStu-A141 P; *Pseudomonas stutzeri* maltotetrahydrolase amino acid sequence with P substitution for A residue at position 141. SEQ ID NO: 14 shows the sequence of PStu-G223A; *Pseudomonas stutzeri* maltotetrahydrolase amino acid sequence with A substitution for G residue at position 223. SEQ ID NO: 15 shows the sequence of PStu-A268P; *Pseudomonas stutzeri* maltotetrahydrolase amino acid sequence with P substitution for A residue at position 268. SEQ ID NO: 16 shows the sequence of PStu-G313P; *Pseudomonas stutzeri* maltotetrahydrolase amino acid sequence with P substitution for G residue at position 313. SEQ ID NO: 17 shows the sequence of PStu-S399P; *Pseudomonas stutzeri* maltotetrahydrolase amino acid sequence with P substitution for S residue at position 399. SEQ ID NO: 18 shows the sequence of PStu-G400P; *Pseudomonas stutzeri* maltotetrahydrolase amino acid sequence with P substitution for G residue at position 400.

SEQ ID NO: 19 shows the sequence of *Pseudomonas stutzeri* (*Pseudomonas perfectomarina*). Glucan 1,4-alpha-maltotetrahydrolase precursor (EC 3.2.1.60) (G4-amylase) (Maltotetraose-forming amylase) (Exo-maltotetraohydrolase)(Maltotetraose-forming exo-amylase). SWISS-PROT accession number P13507.

SEQ ID NO: 20 shows the sequence of *Pseudomonas stutzeri* maltotetrahydrolase nucleic acid sequence. *P. stutzeri* maltotetraose-forming amylase (amyP) gene, complete cds. GenBank accession number M24516.

DETAILED DESCRIPTION

PS4 Variants

We provide for polypeptides, and nucleic acids encoding these, which are variants of polypeptides having non-maltogenic exoamylase activity. Such variant polypeptides are referred to in this document as "PS4 variant polypeptides", and the nucleic acids as "PS4 variant nucleic acids". PS4 variant polypeptides and nucleic acids will be described in further detail below.

Specifically, we provide for PS4 variant polypeptides with sequence alterations comprising proline or alanine substitutions, or both, in a non-maltogenic exoamylase sequence.

Such variant polypeptides retain at least some of the features of the parent polypeptides, and additionally preferably have additional beneficial properties, for example, enhanced activity or thermostability, or pH resistance, or any combination (preferably all). The PS4 substitution mutants described here may preferably be used for any purpose for which the parent enzyme is suitable. In particular, they may be used in any application for which exo-maltotetraohydrolase is used. In highly preferred embodiments, they have the added advantage of higher thermostability, or higher pH stability, or both. Examples of suitable uses for the PS4 variant polypeptides and nucleic acids include food production, in particular baking, as well as production of foodstuffs and feedstuffs; further examples are set out in detail below.

The "parent" sequences, i.e., the sequences on which the PS4 variant polypeptides and nucleic acids are based, preferably are polypeptides having non-maltogenic exoamylase activity. The terms "parent enzymes" and "parent polypeptides" should be interpreted accordingly, and taken to mean the enzymes and polypeptides on which the PS4 variant polypeptides are based.

In particularly preferred embodiments, the parent sequences are non-maltogenic exoamylase enzymes, preferably bacterial non-maltogenic exoamylase enzymes. In highly preferred embodiments, the parent sequence comprises a glucan 1,4-alpha-maltotetrahydrolase (EC 3.2.1.60). Preferably, the parent sequence is from *Pseudomonas* species, for example *Pseudomonas saccharophilia* or *Pseudomonas stutzeri*.

In preferred embodiments, the parent polypeptide comprises, or is homologous to, a *Pseudomonas saccharophilia* non-maltogenic exoamylase having a sequence shown as SEQ ID NO: 1. Proteins and nucleic acids related to, preferably having sequence or functional homology with *Pseudomonas saccharophilia* non-maltogenic exoamylase *Pseudomonas saccharophilia* exoamylase sequence shown as SEQ ID NO: 1 are referred to in this document as members of the "PS4 family". Examples of "PS4 family" non-maltogenic exoamylase enzymes suitable for use in generating the PS4 variant polypeptides and nucleic acids are disclosed in further detail below.

In some preferred embodiments, the parent polypeptide comprises a non-maltogenic exoamylase from *Pseudomonas saccharophilia* non-maltogenic exoamylase having a sequence shown as SEQ ID NO: 1, or a SWISS-PROT accession number P22963. In other preferred embodiments, the parent polypeptide comprises a non-maltogenic exoamylase from *Pseudomonas stutzeri* having a sequence shown as SEQ ID NO: 11, or a *Pseudomonas stutzeri* non-maltogenic exoamylase having SWISS-PROT accession number P13507.

The PS4 variant polypeptides and nucleic acids vary from their parent sequences by including one or more mutations. In other words, the sequence of the PS4 variant polypeptide or nucleic acid is different from that of its parent at one or more positions or residues. In preferred embodiments, the mutations comprise amino acid substitutions, that is, a change of one amino acid residue for another. Thus, the PS4 variant polypeptides comprise one or more changes in the nature of the amino acid residue at one or more positions of the parent sequence.

In describing the different PS4 variant polypeptide variants produced or which are contemplated to be encompassed by this document, the following nomenclature will be adopted for ease of reference: [original amino acid/position according to the numbering system/substituted amino acid]. Accordingly, for example, the substitution of alanine with proline in position 141 is designated as A141P. Multiple mutations are separated by slash marks "/", e.g. A141P/G223A representing mutations in position 141 and 223 substituting alanine with proline and glycine with alanine respectively.

All positions referred to in the present document by numbering refer to the numbering of a *Pseudomonas saccharophilia* exoamylase reference sequence shown below (SEQ ID NO: 1):

```
  1 DQAGKSPAGV RYHGGDEIIL QGFHWNVVRE APNDWYNILR QQASTIAADG FSAIWMPVPW
 61 RDFSSWTDGG KSGGGEGYFW HDFNKNGRYG SDAQLRQAAG ALGGAGVKVL YDVVPNHMNR
121 GYPDKEINLP AGQGFWRNDC ADPGNYPNDC DDGDRFIGGE SDLNTGHPQI YGMFRDELAN
181 LRSGYGAGGF RFDFVRGYAP ERVDSWMSDS ADSSFCVGEL WKGPSEYPSW DWRNTASWQQ
241 IIKDWSDRAK CPVFDFALKE RMQNGSVADW KHGLNGNPDP RWREVAVTFV DNHDTGYSPG
301 QNGGQHHWAL QDGLIRQAYA YILTSPGTPV VYWSHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGGE GGLVNVNFRC DNGVTQMGDS VYAVGNVSQL GNWSPASAVR LTDTSSYPTW
481 KGSIALPDGQ NVEWKCLIRN EADATLVRQW QSGGNNQVQA AAGASTSGSF
```

The reference sequence is derived from the *Pseudomonas saccharophilia* sequence having SWISS-PROT accession number P22963, but without the signal sequence MSHILRAAVLAAVLLPFPALA (SEQ ID NO: 21).

The PS4 variant polypeptide variants described here preferably comprise one or more amino acid substitutions selected from the group consisting of 69P, A141P, G223A, A268P, G313P, S399P and G400P. In one embodiment, the PS4 variants are derived from a *Pseudomonas saccharophila* non-maltogenic enzyme sequence. Accordingly, and preferably, the PS4 variant polypeptide variants are preferably selected from the group consisting of: PSac-69P (SEQ ID NO: 2), PSac-A141P (SEQ ID NO: 3), PSac-G223A (SEQ ID NO: 4), PSac-A268P (SEQ ID NO: 5), PSac-G313P (SEQ ID NO: 6), PSac-S399P (SEQ ID NO: 7) and PSac-G400P (SEQ ID NO: 8).

In highly preferred embodiments, we provide for a PSac-A141P PS4 variant polypeptide having a sequence shown as SEQ ID NO: 3.

In another embodiment, the PS4 variants are derived from a *Pseudomonas stutzeri* non-maltogenic enzyme sequence, preferably shown as SEQ ID NO: 11 below:

```
  1 DQAGKSPNAV RYHGGDEIIL QGFHWNVVRE APNDWYNILR QQAATIAADG FSAIWMPVPW
 61 RDFSSWSDGS KSGGGEGYFW HDFNKNGRYG SDAQLRQAAS ALGGAGVKVL YDVVPNHMNR
121 GYPDKEINLP AGQGFWRNDC ADPGNYPNDC DDGDRFIGGD ADLNTGHPQV YGMFRDEFTN
```

```
-continued
181 LRSQYGAGGF RFDFVRGYAP ERVNSWMTDS ADNSFCVGEL WKGPSEYPNW DWRNTASWQQ

241 IIKDWSDRAK CPVFDFALKE RMQNGSIADW KHGLNGNPDP RWREVAVTFV DNHDTGYSPG

301 QNGGQHHWAL QDGLIRQAYA YILTSPGTPV VYWSHMYDWG YGDFIRQLIQ VRRAAGVRAD

361 SAISFHSGYS GLVATVSGSQ QTLVVALNSD LGNPGQVASG SFSEAVNASN GQVRVWRSGT

421 GSGGGEPGAL VSVSFRCDNG ATQMGDSVYA VGNVSQLGNW SPAAALRLTD TSGYPTWKGS

481 IALPAGQNEE WKCLIRNEAN ATQVRQWQGG ANNSLTPSEG ATTVGRL
```

Accordingly, and preferably, the PS4 polypeptide variants are preferably selected from the group consisting of: PStu-69P (SEQ ID NO: 12), PStu-A141P (SEQ ID NO: 13), PStu-G223A (SEQ ID NO: 14), PStu-A268P (SEQ ID NO: 15), PStu-G313P (SEQ ID NO: 16), PStu-S399P (SEQ ID NO: 17) and PStu-G400P (SEQ ID NO: 18).

In highly preferred embodiments, we provide for a PStu-A141P PS4 variant polypeptide having a sequence shown as SEQ ID NO: 13.

In the context of the present description a specific numbering of amino acid residue positions in PS4 exoamylase enzymes is employed. Preferably, all positions referred to in the present document by numbering refer to the numbering of a *Pseudomonas saccharophilia* exoamylase reference sequence shown below (SEQ ID NO: 1).

In this respect, by alignment of the amino acid sequences of various known exoamylases it is possible to unambiguously allot a exoamylase amino acid position number to any amino acid residue position in any exoamylase enzyme, the amino acid sequence of which is known.

Using this numbering system originating from for example the amino acid sequence of the exoamylase obtained from *Pseudomonas saccharophilia*, aligned with amino acid sequences of a number of other known exoamylase, it is possible to indicate the position of an amino acid residue in a exoamylase unambiguously.

Therefore, the numbering system, even though it may use a specific sequence as a base reference point, is also applicable to all relevant homologous sequences. For example, the position numbering may be applied to homologous sequences from other *Pseudomonas* species, or homologous sequences from other bacteria. Preferably, such homologous have 60% or greater homology, for example 70% or more, 80% or more, 90% or more or 95% or more homology, with the reference sequence SEQ ID NO: 1 above, or the sequences having SWISS-PROT accession numbers P22963 or P13507, preferably with all these sequences. Sequence homology between proteins may be ascertained using well known alignment programs and hybridisation techniques described herein. Such homologous sequences will be referred to in this document as the "PS4 Family".

Furthermore, and as noted above, the numbering system used in this document makes reference to a reference sequence SEQ ID NO: 1, which is derived from the *Pseudomonas saccharophilia* sequence having SWISS-PROT accession number P22963, but without the signal sequence MSHILRAAVLAAVLLPFPALA (SEQ ID NO: 21). This signal sequence is located N terminal of the reference sequence and consists of 21 amino acid residues. Accordingly, it will be trivial to identify the particular residues to be mutated or substituted in corresponding sequences comprising the signal sequence, or indeed, corresponding sequences comprising any other N- or C-terminal extensions or deletions. For example, the sequence of *Pseudomonas saccharophilia* non-maltogenic exoamylase having SWISS-PROT accession number P22963 or a *Pseudomonas stutzeri* non-maltogenic exoamylase having SWISS-PROT accession number P13507.

The PS4 variant polypeptides may comprise one or more of the mutations set out above; in some aspects, there is just one mutation. In other aspects there are two mutations. In particular, they may comprise any pair of such mutations. In further aspects there are three mutations. In other aspects there are more than three mutations. They may comprise any combination of three, four, five, six, seven or more of the mutations as set out.

In particularly preferred embodiments, where there is more than one mutation, the PS4 variant polypeptides comprise the substitutions A141P or G223A, or both. We therefore disclose PS4 variant polypeptides which comprise A141P together with at least one other mutation. We also disclose PS4 variant polypeptides which comprise G223A together with at least one other mutation. In particular, we disclose a PS4 variant polypeptide comprising A141P as well as G223A, i.e., A141P/G223P.

Other mutations, such as deletions, insertions, substitutions, transversions, transitions and inversions, at one or more other locations, may also be included.

We also provide PS4 nucleic acids having sequences which correspond to or encode the alterations in the PS4 variant polypeptide sequences. The skilled person will be aware of the relationship between nucleic acid sequence and polypeptide sequence, in particular, the genetic code and the degeneracy of this code, and will be able to construct such PS4 nucleic acids without difficulty. For example, he will be aware that for each amino acid substitution in the PS4 variant polypeptide sequence, there may be one or more codons which encode the substitute amino acid. Accordingly, it will be evident that, depending on the degeneracy of the genetic code with respect to that particular amino acid residue, one or more PS4 nucleic acid sequences may be generated corresponding to that PS4 variant polypeptide sequence. Furthermore, where the PS4 variant polypeptide comprises more than one substitution, for example A 141 P/G223A, the corresponding PS4 nucleic acids may comprise pairwise combinations of the codons which encode respectively the two amino acid changes.

Thus, for example, PS4 variant nucleic acid sequences may comprise a codon CCA, CCC, CCG or CCT, at any one or more of positions 207–209, 423–425, 804–806, 939–941, 1197–1199, 1200–1202, and/or a codon GCA, GCC, GCG or GCT at positions 669–671, with reference to the position numbering of a *Pseudomonas saccharophilia* exoamylase nucleotide sequence with GenBank accession number X16732, or as shown as SEQ ID NO: 10. Preferably, the position numbering is with reference to the sequence shown as SEQ ID NO: 10. Corresponding *Pseudomonas stutzeri* non-maltogenic exoamylase variants can similarly be constructed.

It will be understood that nucleic acid sequences which are not identical to the particular PS4 variant nucleic acid sequences, but are related to these, will also be useful for the methods and compositions described here. Accordingly, it will be understood that the following are included: (a) a nucleotide sequence that is a variant, homologue, derivative or fragment of a PS4 variant nucleic acid sequence; (b) a nucleotide sequence that is the complement of a PS4 variant nucleic acid sequence; (c) a nucleotide sequence that is the complement of a variant, homologue, derivative or fragment of a PS4 variant nucleic acid sequence; (d) a nucleotide sequence that is capable of hybridising to a PS4 variant nucleic acid sequence; (e) a nucleotide sequence that is capable of hybridising to a variant, homologue, derivative or fragment of a PS4 variant nucleic acid sequence; (f) a nucleotide sequence that is the complement of a nucleotide sequence that is capable of hybridising to a PS4 variant nucleic acid sequence; (g) a nucleotide sequence that is the complement of a nucleotide sequence that is capable of hybridising to a variant, homologue, derivative or fragment of a PS4 variant nucleic acid sequence; (h) a nucleotide sequence that is capable of hybridising to the complement of a PS4 variant nucleic acid sequence; and (i) a nucleotide sequence that is capable of hybridising to the complement of a variant, homologue, derivative or fragment of a PS4 variant nucleic acid sequence. Unless the context dictates otherwise, the term "PS4 variant nucleic acid" should be taken to include each of these entities listed above.

Mutations in amino acid sequence and nucleic acid sequence may be made by any of a number of techniques, as known in the art. In particularly preferred embodiments, the mutations are introduced into parent sequences by means of PCR (polymerase chain reaction) using appropriate primers, as illustrated in the Examples. It is therefore possible to alter the sequence of a polypeptide by introducing an amino acid substitution selected from the group consisting of: G69P, A141P, G223A, A268P, G313P, S399P and G400P into a parent polypeptide having non-maltogenic exoamylase activity, into a *Pseudomonas saccharophilia* or a *Pseudomonas stutzeri* exoamylase sequence at amino acid or nucleic acid level, as described. However, as noted elsewhere, this sequence does not itself need to comprise a wild type sequence; rather, it can be an already mutated sequence.

Furthermore, it will of course be appreciated that the PS4 variant polypeptide does not need in fact to be actually derived from a wild type polypeptide or nucleic acid sequence by, for example, step by step mutation. Rather, once the sequence of the PS4 variant polypeptide is established, the skilled person can easily make that sequence from the wild type with all the mutations, via means known in the art, for example, using appropriate oligonucleotide primers and PCR. In fact, the PS4 variant polypeptide can be made de novo with all its mutations, through, for example, peptide synthesis methodology.

In general, however, the PS4 variant polypeptides and/or nucleic acids are derived or derivable from a "precursor" sequence. The term "precursor" as used herein means an enzyme that precedes the enzyme which is modified according to the methods and compositions described here. Thus, the precursor may be an enzyme that is modified by mutagenesis as described elsewhere in this document. Likewise, the precursor may be a wild type enzyme, a variant wild type enzyme or an already mutated enzyme.

We further describe a method in which the sequence of a non-maltogenic exoamylase is altered by altering the sequence of a nucleic acid which encodes the non-maltogenic exoamylase.

The PS4 variant polypeptides and nucleic acids may be produced by any means known in the art. Specifically, they may be expressed from expression systems, which may be in vitro or in vivo in nature. Specifically, we provide for plasmids and expression vectors comprising PS4 nucleic acid sequences, preferably capable of expressing PS4 variant polypeptides. Cells and host cells which comprise and are preferably transformed with such PS4 nucleic acids, plasmids and vectors are also disclosed, and it should be made clear that these are also encompassed in this document.

In preferred embodiments, the PS4 variant nucleic acid or polypeptide sequence is in an isolated form. The term "isolated" means that the sequence is at least substantially free from at least one other component with which the sequence is naturally associated in nature and as found in nature. In one aspect, preferably the sequence is in a purified form. The term "purified" means that the sequence is in a relatively pure state—e.g. at least about 90% pure, or at least about 95% pure or at least about 98% pure.

We further disclose a construct comprising a PS4 variant nucleotide sequence; a vector comprising PS4 variant nucleotide sequence; a plasmid comprising PS4 variant nucleotide sequence; a transformed cell comprising a PS4 variant nucleotide sequence; a transformed tissue comprising a PS4 variant nucleotide sequence; a transformed organ comprising a PS4 variant nucleotide sequence; a transformed host comprising a PS4 variant nucleotide sequence; a transformed organism comprising a PS4 variant nucleotide sequence. We also disclose methods of expressing a PS4 variant nucleotide sequence, such as expression in a host cell; including methods for transferring same. We also disclose methods of isolating the PS4 variant nucleotide sequence, such as isolating from a host cell.

Other aspects concerning a variant PS4 amino acid sequence include: a construct encoding a variant PS4 amino acid sequence; a vector encoding a variant PS4 amino acid sequence; a plasmid encoding a variant PS4 amino acid sequence; a transformed cell expressing a variant PS4 amino acid sequence; a transformed tissue expressing a variant PS4 amino acid sequence; a transformed organ expressing a variant PS4 amino acid sequence; a transformed host expressing a variant PS4 amino acid sequence; a transformed organism expressing a variant PS4 amino acid sequence. We also disclose methods of purifying the amino acid sequence for use in the methods and compositions described here, such as expression in a host cell; including methods of transferring same, and then purifying said sequence.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1–3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Prin-*

*ciples and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Baca Raton, Fla., 1988, ISBN 0-8493-6078-1, John D. Pound (ed); "*Immunochemical Protocols, vol 80*", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

Parent Enzyme

The PS4 variant polypeptides are derived from, or are variants of, another sequence, known as a "parent enzyme", a "parent polypeptide" or a "parent sequence".

The term "parent enzyme" as used in this document means the enzyme that has a close, preferably the closest, chemical structure to the resultant variant, i.e., the PS4 variant polypeptide or nucleic acid. The parent enzyme may be a precursor enzyme (i.e. the enzyme that is actually mutated) or it may be prepared de novo. The parent enzyme may be a wild type enzyme.

The term "precursor" as used herein means an enzyme that precedes the enzyme which is modified to produce the enzyme. Thus, the precursor may be an enzyme that is modified by mutagenesis. Likewise, the precursor may be a wild type enzyme, a variant wild type enzyme or an already mutated enzyme.

The term "wild type" is a term of the art understood by skilled persons and means a phenotype that is characteristic of most of the members of a species occurring naturally and contrasting with the phenotype of a mutant. Thus, in the present context, the wild type enzyme is a form of the enzyme naturally found in most members of the relevant species. Generally, the relevant wild type enzyme in relation to the variant polypeptides described here is the most closely related corresponding wild type enzyme in terms of sequence homology.

However, where a particular wild type sequence has been used as the basis for producing a variant PS4 polypeptide as described here, this will be the corresponding wild type sequence regardless of the existence of another wild type sequence that is more closely related in terms of amino acid sequence homology.

The parent enzyme is preferably a polypeptide which preferably exhibits non-maltogenic exoamylase activity. Preferably, the parent enzyme is a non-maltogenic exoamylase itself. For example, the parent enzyme may be a *Pseudomonas saccharophila* non-maltogenic exoamylase, such as a polypeptide having SWISS-PROT accession number P22963, or a *Pseudomonas stutzeri* non-maltogenic exoamylase, such as a polypeptide having SWISS-PROT accession number P13507. Other members of the PS4 family may be used as parent enzymes; such PS4 family members will generally be similar to, homologous to, or functionally equivalent to either of these two enzymes, and may be identified by standard methods, such as hybridisation screening of a suitable library using probes, or by genome sequence analysis.

In particular, functional equivalents of either of these two enzymes, as well as other members of the "PS4 family" may also be used as starting points or parent polypeptides for the generation of PS4 variant polypeptides as described here.

The term "functional equivalent" in relation to a parent enzyme being a *Pseudomonas saccharophila* non-maltogenic exoamylase, such as a polypeptide having SWISS-PROT accession number P22963, or a *Pseudomonas stutzeri* non-maltogenic exoamylase, such as a polypeptide having SWISS-PROT accession number P13507 means that the functional equivalent could be obtained from other sources. The functionally equivalent enzyme may have a different amino acid sequence but will have in general have some non-maltogenic exoamylase activity.

In highly preferred embodiments, the functional equivalent will have sequence homology to either of the *Pseudomonas saccharophila* and *Pseudomonas stutzeri* non-maltogenic exoamylases mentioned above, preferably both. The functional equivalent may also have sequence homology with any of the sequences set out as SEQ ID NOs: 1 to 20, preferably SEQ ID NO: 1 or SEQ ID NO: 11 or both. Sequence homology between such sequences is preferably at least 60%, preferably 65% or more, preferably 75% or more, preferably 80% or more, preferably 85% or more, preferably 90% or more, preferably 95% or more. Such sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid —Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However it is preferred to use the GCG Bestfit program.

In other embodiments, the functional equivalents will be capable of specifically hybridising to any of the sequences set out above. Methods of determining whether one sequence is capable of hybridising to another are known in the art, and are for example described in Sambrook, et al (supra) and Ausubel, F. M. et al. (supra). In highly preferred embodiments, the functional equivalents will be capable of hybridising under stringent conditions, e.g. 65° C. and 0.1×SSC {1×SSC=0.15 M NaCl, 0.015 M $Na_3$ Citrate pH 7.0}.

The parent enzymes may be modified at the amino acid level or the nucleic acid level to generate the PS4 variant sequences described here. Therefore, we provide for the generation of G69P, A141P, G223A, A268P, G313P, S399P or G400P amino acid sequence variants (i.e., PS4 variant polypeptides), by introducing one or more corresponding codon changes in the nucleotide sequence encoding a non-maltogenic exoamylase polypeptide. Preferably, such changes include one or more of codon substitutions CCA, CCC, CCG or CCT, at any one or more of positions 207–209, 423–425, 804–806, 939–941, 1197–1199, 1200–1202, and/or a codon GCA, GCC, GCG or GCT at positions 669–671, in any PS4 family nucleic acid sequence, for example, a *Pseudomonas saccharophila* or a *Pseudomonas stutzeri* non-maltogenic exoamylase nucleic acid sequence (e.g., X16732 or M24516).

The nucleic acid numbering should preferably be with reference to the position numbering of a *Pseudomonas saccharophilia* exoamylase nucleotide sequence shown as SEQ ID NO: 10. Alternatively, or in addition, reference may be made to the sequence with GenBank accession number X16732. In preferred embodiments, the nucleic acid numbering should be with reference to the nucleotide sequence shown as SEQ ID NO: 10. However, as with amino acid residue numbering, the residue numbering of this sequence is to be used only for reference purposes only. In particular, it will be appreciated that the above codon changes can be made in any PS4 family nucleic acid sequence. For example, sequence changes can be made to a *Pseudomonas saccharophila* or a *Pseudomonas stutzeri* non-maltogenic exoamylase nucleic acid sequence (e.g., X16732, SEQ ID NO: 10 or M24516, SEQ ID NO: 20).

Amylase

The PS4 variant polypeptides generally comprise amylase activity.

The term "amylase" is used in its normal sense—e.g. an enzyme that is inter alia capable of catalysing the degradation of starch. In particular they are hydrolases which are capable of cleaving α-D-(1→4) O-glycosidic linkages in starch.

Amylases are starch-degrading enzymes, classified as hydrolases, which cleave α-D-(1→4) O-glycosidic linkages in starch. Generally, α-amylases (E.C. 3.2.1.1, α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (E.C. 3.2.1.2, α-D-(1→4)-glucan maltohydrolase), and some product-specific amylases cleave the starch molecule from the non-reducing end of the substrate. β-Amylases, α-glucosidases (E.C. 3.2.1.20, α-D-glucoside glucohydrolase), glucoamylase (E.C. 3.2.1.3, α-D-(1→4)-glucan glucohydrolase), and product-specific amylases can produce maltooligosaccharides of a specific length from starch.

Non-maltogenic Exoamylase

The PS4 variant polypeptides described in this document are derived from (or variants of) polypeptides which preferably exhibit non-maltogenic exoamylase activity. Preferably, these parent enzymes are non-maltogenic exoamylases themselves. The PS4 variant polypeptides themselves in highly preferred embodiments also exhibit non-maltogenic exoamylase activity.

In highly preferred embodiments, the term "non-maltogenic exoamylase enzyme" as used in this document should be taken to mean that the enzyme does not initially degrade starch to substantial amounts of maltose as analysed in accordance with the product determination procedure as described in this document.

In highly preferred embodiments, the non-maltogenic exoamylase comprises an exo-maltotetraohydrolase. Exo-maltotetraohydrolase (E.C.3.2.1.60) is more formally known as glucan 1,4-alpha-maltotetrahydrolase. This enzyme hydrolyses 1,4-alpha-D-glucosidic linkages in amylaceous polysaccharides so as to remove successive maltotetraose residues from the non-reducing chain ends.

Assays for Non-Maltogenic Exoamylase Activity

The following system is used to characterize polypeptides having non-maltogenic exoamylase activity which are suitable for use according to the methods and compositions described here. This system may for example be used to characterise the PS4 parent or variant polypeptides described here.

By way of initial background information, waxy maize amylopectin (obtainable as WAXILYS 200 from Roquette, France) is a starch with a very high amylopectin content (above 90%). 20 mg/ml of waxy maize starch is boiled for 3 min. in a buffer of 50 mM MES (2-(N-morpholino) ethanesulfonic acid), 2 mM calcium chloride, pH 6.0 and subsequently incubated at 50□C. and used within half an hour.

One unit of the non-maltogenic exoamylase is defined as the amount of enzyme which releases hydrolysis products equivalent to 1 μmol of reducing sugar per min. when incubated at 50 degrees C. in a test tube with 4 ml of 10 mg/ml waxy maize starch in 50 mM MES, 2 mM calcium chloride, pH 6.0 prepared as described above. Reducing sugars are measured using maltose as standard and using the dinitrosalicylic acid method of Bernfeld, *Methods Enzymol.*, (1954), 1, 149–158 or another method known in the art for quantifying reducing sugars.

The hydrolysis product pattern of the non-maltogenic exoamylase is determined by incubating 0.7 units of non-maltogenic exoamylase for 15 or 300 min. at 50□C. in a test tube with 4 ml of 10 mg/ml waxy maize starch in the buffer prepared as described above. The reaction is stopped by immersing the test tube for 3 min. in a boiling water bath.

The hydrolysis products are analyzed and quantified by anion exchange HPLC using a Dionex PA 100 column with sodium acetate, sodium hydroxide and water as eluents, with pulsed amperometric detection and with known linear maltooligosaccharides of from glucose to maltoheptaose as standards. The response factor used for maltooctaose to maltodecaose is the response factor found for maltoheptaose.

Preferably, the PS4 parent polypeptides (and the PS4 variant polypeptides) have non-maltogenic exoamylase activity such that if an amount of 0.7 units of said non-maltogenic exoamylase were to incubated for 15 minutes at a temperature of 50° C. at pH 6.0 in 4 ml of an aqueous solution of 10 mg preboiled waxy maize starch per ml buffered solution containing 50 mM 2-(N-morpholino) ethane sulfonic acid and 2 mM calcium chloride then the enzyme would yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis products would consist of linear maltooligosaccharides of from three to ten D-glucopyranosyl units, preferably of linear maltooligosaccharides consisting of from four to eight D-glucopyranosyl units.

For ease of reference, and for the present purposes, the feature of incubating an amount of 0.7 units of the non-maltogenic exoamylase for 15 minutes at a temperature of 50° C. at pH 6.0 in 4 ml of an aqueous solution of 10 mg preboiled waxy maize starch per ml buffered solution containing 50 mM 2-(N-morpholino)ethane sulfonic acid and 2 mM calcium chloride, may be referred to as the "Waxy Maize Starch Incubation Test".

The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

As used herein, the term "linear malto-oligosaccharide" is used in the normal sense as meaning 2–10 units of α-D-glucopyranose linked by an α-(1→4) bond.

Thermostability and pH Stability

Preferably, the PS4 variant polypeptide is thermostable; preferably, it has higher thermostability than its parent enzyme.

As used herein the term 'thermostable' relates to the ability of the enzyme to retain activity after exposure to elevated temperatures. Preferably, the PS4 variant polypeptide is capable of degrading resistant starch at temperatures of from about 20° C. to about 50° C. Suitably, the enzyme retains its activity after exposure to temperatures of up to about 95° C.

The thermostability of an enzyme such as a non-maltogenic exoamylase is measured by its half life. Thus, the PS4 variant polypeptides described here have half lives extended relative to the parent enzyme by preferably 10%, 20%, 30%, 40%, 50%, 60%, 70%, 80%, 90%, 100%, 200% or more. A PS4 variant polypeptide may be one in particular in which the half life ($t_{1/2}$) is increased by 15% or more, preferably 50% or more, most preferably 100% or more, relative to the parent polypeptide, preferably when tested under the same conditions.

As used here, the half life (t½) is the time (in minutes) during which half the enzyme activity is inactivated under defined heat conditions. In preferred embodiments, the half life is assayed at 60 degrees C. Preferably, the sample is heated for 1–10 minutes at 60° C. or higher. The half life value is then calculated by measuring the residual amylase activity, by any of the methods described here. Preferably, a half life assay is conducted as described in more detail in the Examples.

Preferably, the PS4 variant polypeptide is pH stable; more preferably, it has a higher pH stability than its cognate parent polypeptide. As used herein the term 'pH stable' relates to the ability of the enzyme to retain activity over a wide range of pHs. Preferably, the PS4 variant polypeptide is capable of degrading resistant starch at a pH of from about 5 to about 10.5. In one embodiment, the degree of pH stability may be assayed by measuring the half life of the enzyme in specific pH conditions. In another embodiment, the degree of pH stability may be assayed by measuring the activity or specific activity of the enzyme in specific pH conditions. The specific pH conditions may be any pH from pH5 to pH10.5.

Thus, the PS4 variant polypeptide may have a longer half life, or a higher activity (depending on the assay) when compared to the parent polypeptide under identical conditions. The PS4 variant polypeptides may have 10%, 20%, 30%, 40%, 50%, 60%, 70%, 80%, 90%, 100%, 200% or longer half life when compared to their parent polypeptides under identical pH conditions. Alternatively, or in addition, they may have such higher activity when compared to the parent polypeptide under identical pH conditions.

Uses of PS4 Variant Polypeptides and Nucleic Acids

The PS4 variant polypeptides, nucleic acids, host cells, expression vectors, etc, may be used in any application for which an amylase may be used. In particular, they may be used to substitute for any non-maltogenic exoamylase. They may be used to supplement amylase or non-maltogenic exoamylase activity, whether alone or in combination with other known amylases or non-maltogenic exoamylases.

The PS4 variant sequences described here may be used in various applications in the food industry—such as in bakery and drink products, they may also be used in other applications such as a pharmaceutical composition, or even in the chemical industry. In particular, the PS4 variant polypeptides and nucleic acids are useful for various industrial applications including baking (as disclosed in WO 99/50399), flour standardisation (volume enhancement or improvement) as well as feed processing (see below). They may be used to produce maltotetraose from starch and other substrates.

The PS4 variant polypeptides may be used to enhance the volume of foods, including baked foods such as bread. Thus, food products comprising or treated with PS4 variant polypeptides are expanded in volume when compared to products which have not been so treated, or treated with parent polypeptides. In other words, the food products have a larger volume of air per volume of food product. Alternatively, or in addition, the food products treated with PS4 variant polypeptides have a lower density, or weight (or mass) per volume ratio. In particularly preferred embodiments, the PS4 variant polypeptides are used to enhance the volume of bread. Volume enhancement or expansion is beneficial because it reduces the gumminess or starchiness of foods. Light foods are preferred by consumers, and the customer experience is enhanced. In preferred embodiments, the use of PS4 variant polypeptides enhances the volume by 10%, 20%, 30% 40%, 50% or more.

The use of PS4 variant polypeptides to increase the volume of foods is described in detail in Example 10.

Food Uses

The PS4 variant polypeptides and nucleic acids described here may be used as—or in the preparation of—a food. Here, the term "food" is used in a broad sense—and covers food for humans as well as food for animals (i.e. a feed). In a preferred aspect, the food is for human consumption. The food may be in the from of a solution or as a solid—depending on the use and/or the mode of application and/or the mode of administration.

The PS4 variant polypeptides and nucleic acids may be used as a food ingredient. As used herein the term "food ingredient" includes a formulation, which is or can be added to functional foods or foodstuffs and includes formulations which can be used at low levels in a wide variety of products that require, for example, acidifying or emulsifying. The food ingredient may be in the from of a solution or as a solid—depending on the use and/or the mode of application and/or the mode of administration.

The PS4 variant polypeptides and nucleic acids disclosed here may be—or may be added to—food supplements. The PS4 variant polypeptides and nucleic acids disclosed here may be—or may be added to—functional foods. As used herein, the term "functional food" means food which is capable of providing not only a nutritional effect and/or a taste satisfaction, but is also capable of delivering a further beneficial effect to consumer. Although there is no legal definition of a functional food, most of the parties with an interest in this area agree that they are foods marketed as having specific health effects.

The PS4 variant polypeptides may also be used in the manufacture of a food product or a foodstuff. Typical foodstuffs, which also include feedstuffs such as animal feed, include dairy products, meat products, poultry products, fish products and bakery products. Preferably, the foodstuff is a bakery product. Typical bakery (baked) products include bread—such as loaves, rolls, buns, pizza bases etc.—Danish pastry, pretzels, tortillas, cakes, cookies, biscuits, krackers etc.

Retrogradation/Staling

The PS4 variant polypeptides may in general be used in food applications, for example, in the production of foodstuffs, in particular starch products such as baked starch products. In one specific embodiment, the PS4 variant polypeptides are used to prevent detrimental degradation of starch media, in particular, starch gels. In one preferred aspect, we describe the use of such PS4 variant proteins that are capable of retarding the staling of starch. The PS4 variant polypeptides are also capable of retarding the detrimental retrogradation of starch media, such as starch gels.

Most starch granules are composed of a mixture of two polymers: an essentially linear polysaccharide called amylose and a highly branched polysaccharide called amylopectin. Amylopectin is a very large, branched molecule consisting of chains of α-D-glucopyranosyl units joined by (1→4) linkages, wherein said chains are attached by α-D-(1→6) linkages to form branches. Amylopectin is present in all natural starches, constituting about 75% of most common starches. Starches consisting entirely of amylopectin are known as waxy starches, e.g. waxy corn (waxy maize). Amylose is essentially a linear chain of (1→4) linked α-D-glucopyranosyl units having few α-D-(1→6) branches. Most starches contain about 25% amylose.

Starch granules heated in the presence of water undergo an order-disorder phase transition called gelatinization, where liquid is taken up by the swelling granules. Gelatinization temperatures vary for different starches and depend for the native, unmodified starches on their biological source. Upon cooling of freshly baked bread the amylose fraction, within hours, retrogrades to develop a network. This process is beneficial in that it creates a desirable crumb structure with a low degree of firmness and improved slicing properties. More gradually crystallisation of amylopectin takes place within the gelatinised starch granules during the days after baking. In this process amylopectin is believed to reinforce the amylose network in which the starch granules are embedded. This reinforcement leads to increased firmness of the bread crumb. This reinforcement is one of the main causes of bread staling.

As a consequence of detrimental retrogradation, the water-holding capacity of the paste or gel system is changed with important implications on the gel texture and dietary properties. It is known that the quality of baked bread products gradually deteriorates during storage. The crumb loses softness and elasticity and becomes firm and crumbly. This so-called staling is primarily due to the detrimental retrogradation of starch, which is understood to be a transition of the starch gelatinised during baking from an amorphous state to a quasi crystalline state. The increase in crumb firmness is often used as a measure of the staling process of bread.

The rate of detrimental retrogradation or crystallisation of amylopectin depends on the length of the side chains of amylopectin. In accordance with this, cereal amylopectin retrogrades at a slower rate than amylopectin from pea or potato, which has a longer average chain length than cereal amylopectin. Thus, enzymatic hydrolysis of the amylopectin side chains, for example, by PS4 variant polypeptides having non-maltogenic exoamylase activity, can markedly reduce their crystallisation tendencies.

Accordingly, the use of PS4 variant polypeptides as described here when added to the starch at any stage of its processing into a food product, e.g., before during or after baking into bread can retard or impede or slow down the retrogradation. Such use is described in further detail below.

Assays for Measurement of Retrogradation (Inc. Staling)

For evaluation of the antistaling effect of the PS4 variant polypeptides having non-maltogenic exoamylase activity described here, the crumb firmness can be measured 1, 3 and 7 days after baking by means of an Instron 4301 Universal Food Texture Analyzer or similar equipment known in the art.

Another method used traditionally in the art and which is used to evaluate the effect on starch retrogradation of a PS4 variant polypeptide having non-maltogenic exoamylase activity is based on DSC (differential scanning calorimetry). Hereby the melting enthalpy of retrograded amylopectin in bread crumb or crumb from a model system dough baked with or without enzymes (control) is measured. The DSC equipment applied in the described examples is a Mettler-Toledo DSC 820 run with a temperature gradient of 10° C. per min. from 20 to 95° C. For preparation of the samples 10–20 mg of crumb are weighed and transferred into Mettler-Toledo aluminium pans which then are hermetically sealed.

The model system doughs used in the described examples contain standard wheat flour and optimal amounts of water or buffer with or without the non-maltogenic PS4 variant exoamylase. They are mixed in a 10 or 50 g Brabender Farinograph for 6 or 7 min., respectively. Samples of the doughs are placed in glass test tubes (15*0.8 cm) with a lid. These test tubes are subjected to a baking process in a water bath starting with 30 min. incubation at 33° C. followed by heating from 33 to 95° C. with a gradient of 1.1° C. per min. and finally a 5 min. incubation at 95° C. Subsequently, the tubes are stored in a thermostat at 20° C. prior to DSC analysis.

Preparation of Starch Products

We provide the use of PS4 variant polypeptides in the preparation of food products, in particular, starch products. The method comprises forming the starch product by adding a non-maltogenic exoamylase enzyme such as a PS4 variant polypeptide, to a starch medium. If the starch medium is a dough, then the dough is prepared by mixing together flour, water, the non-maltogenic exoamylase which is a PS4 variant polypeptide and optionally other possible ingredients and additives.

The term "starch" should be taken to mean starch per se or a component thereof, especially amylopectin. The term "starch medium" means any suitable medium comprising starch. The term "starch product" means any product that contains or is based on or is derived from starch. Preferably, the starch product contains or is based on or is derived from starch obtained from wheat flour. The term "flour" as used herein is a synonym for the finely-ground meal of wheat or other grain. Preferably, however, the term means flour obtained from wheat per se and not from another grain. Thus, and unless otherwise expressed, references to "wheat flour" as used herein preferably mean references to wheat flour per se as well as to wheat flour when present in a medium, such as a dough.

A preferred flour is wheat flour or rye flour or mixtures of wheat and rye flour. However, dough comprising flour derived from other types of cereals such as for example from rice, maize, barley, and durra are also contemplated. Preferably, the starch product is a bakery product. More preferably, the starch product is a bread product. Even more preferably, the starch product is a baked farinaceous bread product. The term "baked farinaceous bread product" is understood to refer to any baked product based on ground cereals and baked on a dough obtainable by mixing flour, water, and a leavening agent under dough forming conditions. Further components can of course be added to the dough mixture.

Thus, if the starch product is a baked farinaceous bread product (which is a highly preferred embodiment), then the process comprises mixing—in any suitable order—flour, water, and a leavening agent under dough forming conditions and further adding a PS4 variant polypeptide, optionally in the form of a premix. The leavening agent may be a chemical leavening agent such as sodium bicarbonate or any strain of *Saccharomyces cerevisiae* (Baker's Yeast).

The PS4 variant non-maltogenic exoamylase can be added together with any dough ingredient including the water or dough ingredient mixture or with any additive or additive mixture. The dough can be prepared by any conventional dough preparation method common in the baking industry or in any other industry making flour dough based products.

Baking of farinaceous bread products such as for example white bread, bread made from bolted rye flour and wheat flour, rolls and the like is typically accomplished by baking the bread dough at oven temperatures in the range of from 180 to 250° C. for about 15 to 60 minutes. During the baking process a steep temperature gradient (200→120° C.) is prevailing in the outer dough layers where the characteristic crust of the baked product is developed. However, owing to heat consumption due to steam generation, the temperature in the crumb is only close to 100° C. at the end of the baking process.

We therefore describe a process for making a bread product comprising: (a) providing a starch medium; (b) adding to the starch medium a PS4 variant polypeptide as described in this document; and (c) applying heat to the starch medium during or after step (b) to produce a bread product. We also describe a process for making a bread product comprising adding to a starch medium a PS4 variant polypeptide as described.

The non-maltogenic exoamylase PS4 variant polypeptide can be added as a liquid preparation or as a dry pulverulent composition either comprising the enzyme as the sole active component or in admixture with one or more additional dough ingredient or dough additive.

In order to improve further the properties of the baked product and impart distinctive qualities to the baked product further dough ingredients and/or dough additives may be incorporated into the dough. Typically, such further added components may include dough ingredients such as salt, grains, fats and oils, sugar, dietary fibre substances, milk powder, gluten and dough additives such as emulsifiers, other enzymes, hydrocolloids, flavouring agents, oxidising agents, minerals and vitamins.

The emulsifiers are useful as dough strengtheners and crumb softeners. As dough strengtheners, the emulsifiers can provide tolerance with regard to resting time and tolerance to shock during the proofing. Furthermore, dough strengtheners will improve the tolerance of a given dough to variations in the fermentation time. Most dough strengtheners also improve on the oven spring which means the increase in volume from the proofed to the baked goods. Lastly, dough strengtheners will emulsify any fats present in the recipe mixture.

The crumb softening, which is mainly a characteristic of the monoglycerides, is attributed to an interaction between the emulsifier and the amylose fraction of the starch leading to formation of insoluble inclusion complexes with the amylose which will not recrystallize upon cooling and which will not therefore contribute to firmness of the bread crumb.

Improving Composition

We describe improver compositions, which include bread improving compositions and dough improving compositions. These comprise a PS4 variant polypeptide, optionally together with other ingredients such as an emulsifying agent, or a further enzyme, or both. The further enzymes may comprise one or more of: an oxidase, a lipase and a xylanase.

We also provide for the use of such a bread and dough improving compositions in baking. In a further aspect, we provide a baked product or dough obtained from the bread improving composition or dough improving composition. In another aspect, we describe a baked product or dough obtained from the use of a bread improving composition or a dough improving composition.

Dough Preparation

A dough may be prepared by admixing flour, water, a dough improving composition comprising PS4 variant polypeptide (as described above) and optionally other ingredients and additives.

The dough improving composition can be added together with any dough ingredient including the flour, water or optional other ingredients or additives. The dough improving composition can be added before the flour or water or optional other ingredients and additives. The dough improving composition can be added after the flour or water, or optional other ingredients and additives. The dough can be prepared by any conventional dough preparation method common in the baking industry or in any other industry making flour dough based products.

The dough improving composition can be added as a liquid preparation or in the form of a dry powder composition either comprising the composition as the sole active component or in admixture with one or more other dough ingredients or additive.

The amount of the PS4 variant polypeptide non-maltogenic exoamylase that is added is normally in an amount which results in the presence in the finished dough of 50 to 100,000 units per kg of flour, preferably 100 to 50,000 units per kg of flour. Preferably, the amount is in the range of 200 to 20,000 units per kg of flour.

In the present context, 1 unit of the non-maltogenic exoamylase is defined as the amount of enzyme which releases hydrolysis products equivalent to 1 μmol of reducing sugar per min. when incubated at 50° C. in a test tube with 4 ml of 10 mg/ml waxy maize starch in 50 mM MES, 2 mM calcium chloride, pH 6.0 as described hereinafter.

The dough as described here generally comprises wheat meal or wheat flour and/or other types of meal, flour or starch such as corn flour, corn starch, maize flour, rice flour, rye meal, rye flour, oat flour, oat meal, soy flour, sorghum meal, sorghum flour, potato meal, potato flour or potato starch. The dough may be fresh, frozen, or part-baked.

The dough may be a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may also comprise other conventional dough ingredients, e.g.: proteins, such as milk powder, gluten, and soy; eggs (either whole eggs, egg yolks or egg white); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat such as granulated fat or shortening. The dough may further comprise a further emulsifier such as mono- or diglycerides, sugar esters of fatty acids, polyglycerol esters of fatty acids, lactic acid esters of monoglycerides, acetic acid esters of monoglycerides, polyoxethylene stearates, or lysolecithin.

We also describe a pre-mix comprising flour together with the combination as described herein. The pre-mix may contain other dough-improving and/or bread-improving additives, e.g. any of the additives, including enzymes, mentioned herein. For some applications, the flour dough preferably comprises a hard flour.

The term "hard flour" as used herein refers to flour which has a higher protein content such as gluten than other flours and is suitable for the production of, for example, bread. The term "hard flour" as used herein is synonymous with the term "strong flour".

A preferred flour for some applications is wheat flour. However doughs comprising flour derived from, for example, maize, corn, oat, barley, rye, durra, rice, soy, sorghum and potato are also contemplated. Preferably the flour dough comprises a hard wheat flour.

Further Dough Additives or Ingredients

One or more additives or further ingredients may be added to the dough.

Typically, further dough additives or ingredients (components) include conventionally used dough additives or ingredients such as salt, sweetening agents such as sugars, syrups or artificial sweetening agents, lipid substances including shortening, margarine, butter or an animal or vegetable oil, glycerol and one or more dough additives such as emulsifying agents, starch degrading enzymes, cellulose or hemicellulose degrading enzymes, proteases, non-specific oxidising agents such as those mentioned above, flavouring agents, lactic acid bacterial cultures, vitamins, minerals, hydrocolloids such as alginates, carrageenans, pectins, vegetable gums including e.g. guar gum and locust bean gum, and dietary fibre substances.

Suitable emulsifiers which may be used as further dough additives include lecithin, polyoxyethylene stearat, mono- and diglycerides of edible fatty acids, acetic acid esters of mono- and diglycerides of edible fatty acids, lactic acid esters of mono- and diglycerides of edible fatty acids, citric acid esters of mono- and diglycerides of edible fatty acids, diacetyl tartaric acid esters of mono- and diglycerides of edible fatty acids, sucrose esters of edible fatty acids, sodium stearoyl-2-lactylate, and calcium stearoyl-2-lactylate.

The further dough additive or ingredient can be added together with any dough ingredient including the flour, water or optional other ingredients or additives, or the dough improving composition. The further dough additive or ingredient can be added before the flour, water, optional other ingredients and additives or the dough improving composition. The further dough additive or ingredient can be added after the flour, water, optional other ingredients and additives or the dough improving composition.

The further dough additive or ingredient may conveniently be a liquid preparation. However, the further dough additive or ingredient may be conveniently in the form of a dry composition.

Preferably the further dough additive or ingredient is selected from the group consisting of a vegetable oil, a vegetable fat, an animal fat, shortening, glycerol, margarine, butter, butterfat and milk fat.

Preferably the further dough additive or ingredient is at least 1% the weight of the flour component of dough. More preferably, the further dough additive or ingredient is at least 2%, preferably at least 3%, preferably at least 4%, preferably at least 5%, preferably at least 6%. If the additive is a fat, then typically the fat may be present in an amount of from 1 to 5%, typically 1 to 3%, more typically about 2%.

Further Enzyme

In addition to the PS4 variant polypeptides, one or more further enzymes may be used, for example added to the dough preparation, foodstuff or starch composition or feed.

Other enzymes which are useful as further dough additives include as examples oxidoreductases, maltose oxidising enzymes, glucose oxidase, hexose oxidase, pyranose oxidase and ascorbate oxidase, hydrolases, such as lipases (see below) and esterases as well as glycosidases like α-amylase, pullulanase, and xylanase. Oxidoreductases, such as for example glucose oxidase and hexose oxidase, can be used for dough strengthening and control of volume of the baked products and xylanases and other hemicellulases may be added to improve dough handling properties, crumb softness and bread volume. Lipases are useful as dough strengtheners and crumb softeners and α-amylases and other amylolytic enzymes may be incorporated into the dough to control bread volume and further reduce crumb firmness. Further details of lipases are set out below.

Further enzymes that may be used may be selected from the group consisting of a xylanase, a cellulase, a hemicellulase, a starch degrading enzyme, a protease, a lipoxygenase, an oxidoreductase, such as a maltose oxidising enzyme, a lipase and an oxidising enzyme such as any one or more of glucose oxidase (EC 1.1.3.4), carbohydrate oxidase, glycerol oxidase, pyranose oxidase (EC 1.1.3.10) and hexose oxidase (EC 1.1.3.5).

Among starch degrading enzymes, amylases are particularly useful as dough improving additives. α-amylase breaks downs starch into dextrins which are further broken down by β-amylase to maltose. Other useful starch degrading enzymes which may be added to a dough composition include glucoamylases and pullulanases.

Preferably, the further enzyme is at least a xylanase and/or at least an amylase. The term "xylanase" as used herein refers to xylanases (EC 3.2.1.32) which hydrolyse xylosidic linkages.

The term "amylase" as used herein refers to amylases such as α-amylases (EC 3.2.1.1), which hydrolyse 1,4-α-D-glucosidic linkages in polysaccharides containing three or more 1,4-α-linked glucose units, β-amylases (EC 3.2.1.2) which hydrolyse 1,4-α-D-glucosidic linkages in polysaccharides so as to remove successive maltose units from the non-reducing ends of the chains, and γ-amylases (EC 3.2.1.3) which hydrolyse the terminal 1,4-linked α-D-glucose residues successively from non-reducing ends of chains with the release of β-D-glucose.

The further enzyme can be added together with any dough ingredient including the flour, water or optional other ingredients or additives, or the dough improving composition. The further enzyme can be added before the flour, water, and optionally other ingredients and additives or the dough improving composition. The further enzyme can be added after the flour, water, and optionally other ingredients and additives or the dough improving composition. The further enzyme may conveniently be a liquid preparation. However, the composition may be conveniently in the form of a dry composition.

Some enzymes of the dough improving composition are capable of interacting with each other under the dough conditions to an extent where the effect on improvement of the Theological and/or machineability properties of a flour dough and/or the quality of the product made from dough by the enzymes is not only additive, but the effect is synergistic.

In relation to improvement of the product made from dough (finished product), it may be found that the combination results in a substantial synergistic effect in respect to crumb homogeneity as defined herein. Also, with respect to the specific volume of baked product a synergistic effect may be found.

The further enzyme may include a "lipase". The term "lipase" as used herein refers to enzymes which are capable of hydrolysing carboxylic ester bonds to release carboxylate (EC 3.1.1). Examples of lipases include but are not limited to triacylglycerol lipase (EC 3.1.1.3), galactolipase (EC 3.1.1.26), phospholipase A1 (EC 3.1.1.32) and phospholipase A2 (EC 3.1.1.4).

The lipase may be isolated and/or purified from natural sources or it may be prepared by use of recombinant DNA techniques. Preferably the lipase is selected from the group comprising triacylglycerol lipase, a galactolipase, phospholipase. In another aspect, the lipase(s) may be one or more of the following: triacylglycerol lipase (EC 3.1.1.3), phospholipase A2 (EC 3.1.1.4), galactolipase (EC 3.1.1.26), phospholipase A1 (EC 3.1.1.32), lipoprotein lipase A2 (EC 3.1.1.34). Lipases are also known as lipolytic enzymes.

Suitable lipases for use in as further enzymes include (but are not limited to) one or more lipase selected from the lipases disclosed in EP0130064, WO 98/26057, WO00/32758, WO 02/03805, and LipopanH, also referred to as Lecitase Ultra™ and HL1232 (LipopanH is disclosed in GRAS Notice 000103, copies of which are available from the Department of Health & Human Services, Food & Drug Administration, Washington D.C. 20204). Each of these references is incorporated herein by reference.

The lipase may in some applications suitably be LipopanF (supplied by Novozymes) or a variant, derivative or homologue thereof.

Other Uses

The PS4 variants are suitable for the production of maltose and high maltose syrups. Such products are of considerable interest in the production of certain confectioneries because of the low hygroscoposity, low viscosity, good heat stability and mild, not too sweet taste of maltose. The industrial process of producing maltose syrups comprises liquefying starch, then saccharification with a maltose producing enzyme, and optionally with an enzyme cleaving the 1.6- branching points in amylopectin, for instance an .alpha.-1.6-amyloglucosidase.

The PS4 variants described here may be added to and thus become a component of a detergent composition. The detergent composition may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific aspect, we describe a detergent additive comprising the PS4 variant. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase. In general the properties of the chosen enzyme(s) should be compatible with the selected detergent, (i.e., pH-optimum, compatibility with other enzymatic and non-enzymatic ingredients, etc.), and the enzyme (s) should be present in effective amounts.

The PS4 variant may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The PS4 variants may especially be useful in a process for producing a papermaking pulp from starch-coated printed paper. The process may be performed as described in WO 95/14807, comprising the following steps: a) disintegrating the paper to produce a pulp, b) treating with a starch-degrading enzyme before, during or after step a), and c) separating ink particles from the pulp after steps a) and b). The PS4 variant may also be very useful in modifying starch where enzymatically modified starch is used in papermaking together with alkaline fillers such as calcium carbonate, kaolin and clays. With the PS4 variants described here it becomes possible to modify the starch in the presence of the filler thus allowing for a simpler integrated process. A PS4 variant may also be very useful in textile desizing. In the textile processing industry, amylases are traditionally used as auxiliaries in the desizing process to facilitate the removal of starch-containing size which has served as a protective coating on weft yarns during weaving. Complete removal of the size coating after weaving is import-ant to ensure optimum results in the subsequent processes, in which the fabric is scoured, bleached and dyed. Enzymatic starch break-down is preferred because it does not involve any harmful effect on the fiber material. The PS4 variant may be used alone or in combination with a cellulase when desizing cellulose-containing fabric or textile.

The PS4 variant may also be an amylase of choice for production of sweeteners from starch A "traditional" process for conversion of starch to fructose syrups normally consists of three consecutive enzymatic processes, viz., a liquefaction process followed by a saccharification process and an isomerization process. During the liquefaction process, starch is degraded to dextrins by an amylase at pH values between 5.5 and 6.2 and at temperatures of 95–160° C. for a period of approx. 2 hours. In order to ensure an optimal enzyme stability under these conditions, 1 mM of calcium is added (40 ppm free calcium ions). After the liquefaction process the dextrins are converted into dextrose by addition of a glucoamylase and a debranching enzyme, such as an isoamylase or a pullulanase. Before this step the pH is reduced to a value below 4.5, maintaining the high temperature (above 95° C.), and the liquefying amylase activity is denatured. The temperature is lowered to 60° C., and glucoamylase and debranching enzyme are added. The saccharification process proceeds for 24–72 hours.

Feed Applications

In one embodiment, the PS4 variant polypeptide is capable of degrading resistant starch.

As used herein the term 'degrading' relates to the partial or complete hydrolysis or degradation of resistant starch to glucose and/or oligosaccharides—such as maltose and/or dextrins.

The PS4 variant polypeptide may degrade residual resistant starch that has not been completely degraded by an animals amylase. By way of example, the PS4 variant polypeptide may be used to assist an animal's amylase (eg. pancreatic amylase) in improving the degradation of resistant starch. Pancreatic α-amylase is excreted in the digestive system by animals. Pancreatic α-amylase degrades starch in the feed. However, a part of the starch, the resistant starch, is not degraded fully by the pancreatic α-amylase and is therefore not absorbed in the small intestine (see definition of resistant starch). The PS4 variant polypeptide in some embodiments is able to assist the pancreatic α-amylase in degrading starch in the digestive system and thereby increase the utilisation of starch by the animal.

The ability of an enzyme to degrade resistant starch may be analysed for example by a method developed and disclosed by Megazyme International Ireland Ltd. for the measurement of resistant starch, solubilised starch and total starch content of a sample (Resistant Starch Assay Procedure, AOAC Method 2002.02, AACC Method 32-40).

Accordingly, the PS4 variant polypeptides may be ingested by an animal for beneficial purposes, and may therefore be incorporated into animal feeds.

We therefore disclose the use of a PS4 variant polypeptide as a component for use in a feed comprising starch, or for use in a feed improvement composition, in which the PS4 variant polypeptide is capable of degrading resistant starch. We also disclose a feed comprising a starch and a PS4 variant polypeptide. We further disclose a method of degrading resistant starch in a feed comprising contacting said resistant starch with a PS4 variant polypeptide.

We further describe the use of a PS4 variant polypeptide in the preparation of a feed comprising a starch, to degrade resistant starch. Furthermore, we disclose the use of a PS4 variant polypeptide in the preparation of a feed to improve the calorific value of said feed. We disclose the use of an enzyme in the preparation of a feed to improve animal performance. In a further embodiment, we describe a process for preparing a feed comprising admixing a starch and a PS4 variant polypeptide enzyme.

By way of example, use of a component comprising PS4 variant polypeptides and which is capable of degrading resistant starch is advantageous because there is a marked increase in the degradation of starch and/or starch degradation products in an animal. Furthermore, such use is advantageous because there is a marked increase in the digestibility of starch and/or starch degradation products by an animal. Furthermore, such use is advantageous because it provides a means of enhancing the efficiency of deriving energy from a feed by an animal. Furthermore, such use is advantageous because it provides a means to enhance the bioavailability of resistant starch.

Animal Feeds

Animal feeds for which the PS4 variant polypeptides are suitable for use may be formulated to meet the specific needs of particular animal groups and to provide the necessary carbohydrate, fat, protein and other nutrients in a form that can be metabolised by the animal.

Preferably, the animal feed is a feed for swine or poultry.

As used herein the term 'swine' relates to non-ruminant omnivores such as pigs, hogs or boars. Typically, swine feed includes about 50 percent carbohydrate, about 20 percent protein and about 5% fat. An example of a high energy swine feed is based on corn which is often combined with feed supplements for example, protein, minerals, vitamins and amino acids such as lysine and tryptophan. Examples of swine feeds include animal protein products, marine products, milk products, grain products and plant protein products, all of which may further comprise natural flavourings, artificial flavourings, micro and macro minerals, animal fats, vegetable fats, vitamins, preservatives or medications such as antibiotics.

It is to be understood that where reference is made in the present specification, including the accompanying claims, to 'swine feed' such reference is meant to include "transition" or "starter" feeds (used to wean young swine) and "finishing" or "grower" feeds (used following the transition stage for growth of swine to an age and/or size suitable for market).

As used herein the term 'poultry' relates to fowl such as chickens, broilers, hens, roosters, capons, turkeys, ducks, game fowl, pullets or chicks. Poultry feeds may be referred to as "complete" feeds because they contain all the protein, energy, vitamins, minerals, and other nutrients necessary for proper growth, egg production, and health of the birds. However, poultry feeds may further comprise vitamins, minerals or medications such as coccidiostats (for example Monensin sodium, Lasalocid, Amprolium, Salinomycin, and Sulfaquinoxaline) and/or antibiotics (for example Penicillin, Bacitracin, Chlortetracycline, and Oxytetracycline).

Young chickens or broilers, turkeys and ducks kept for meat production are fed differently from pullets saved for egg production. Broilers, ducks and turkeys have larger bodies and gain weight more rapidly than do the egg-producing types of chickens. Therefore, these birds are fed diets with higher protein and energy levels.

It is to be understood that where reference is made in the present specification, including the accompanying claims, to 'poultry feed' such reference is meant to include "starter" feeds (post-hatching), "finisher", "grower" or "developer" feeds (from 6–8 weeks of age until slaughter size reached) and "layer" feeds (fed during egg production).

Animal feeds may be formulated to meet the animal's nutritional needs with respect to, for example, meat production, milk production, egg production, reproduction and response to stress. In addition, the animal feeds are formulated to improve manure quality.

In a preferred aspect the animal feed contains a raw material such as a legume, for example pea or soy or a cereal, for example wheat, corn (maize), rye or barley. Suitably, the raw material may be potato.

Feed Stuffs

The PS4 variant polypeptides may be used in feeds for animal consumption by the indirect or direct application of the PS4 variant polypeptides to the feed, whether alone or in combination with other ingredients, such as food ingredients.

Typical food ingredients may include any one or more of an additive such as an animal or vegetable fat, a natural or synthetic seasoning, antioxidant, viscosity modifier, essential oil, and/or flavour, dye and/or colorant, vitamin, mineral, natural and/or non-natural amino acid, nutrient, additional enzyme (including genetically manipulated enzymes), a binding agent such as guar gum or xanthum gum, buffer, emulsifier, lubricant, adjuvant, suspending agent, preservative, coating agent or solubilising agent and the like.

Examples of the application methods include, but are not limited to, coating the feed in a material comprising the PS4 variant polypeptide, direct application by mixing the PS4 variant polypeptide with the feed, spraying the PS4 variant polypeptide onto the feed surface or dipping the feed into a preparation of the PS4 variant polypeptide.

The PS4 variant polypeptide is preferably applied by mixing it with a feed or by spraying onto feed particles for animal consumption. Alternatively, the PS4 variant polypeptide may be included in the emulsion of a feed, or the interior of solid products by injection or tumbling.

The PS4 variant polypeptide may be applied to intersperse, coat and/or impregnate a feed. Mixtures with other ingredients may also be used and may be applied separately, simultaneously or sequentially. Chelating agents, binding agents, emulsifiers and other additives such as micro and macro minerals, amino acids, vitamins, animal fats, vegetable fats, preservatives, flavourings, colourings, may be similarly applied to the feed simultaneously (either in mixture or separately) or applied sequentially.

Amount of PS4 Variant Polypeptide

The optimum amount of the PS4 variant polypeptide to be used will depend on the feed to be treated and/or the method of contacting the feed with the PS4 variant polypeptide and/or the intended use for the same. The amount of PS4 variant polypeptide should be in a sufficient amount to be effective to substantially degrade resistant starch following ingestion and during digestion of the feed.

Advantageously, the PS4 variant polypeptide would remain effective following ingestion of a feed for animal consumption and during digestion of the feed until a more complete digestion of the feed is obtained, i.e. an increased calorific value of the feed is released.

Amylase Combinations

We disclose in particular combinations of PS4 variant polypeptides with amylases, in particular, maltogenic amylases. Maltogenic alpha-amylase (glucan 1,4-a-maltohydrolase, E.C. 3.2.1.133) is able to hydrolyze amylose and amylopectin to maltose in the alpha-configuration, and is also able to hydrolyze maltotriose as well as cyclodextrin.

A maltogenic alpha-amylase from *Bacillus* (EP 120 693) is commercially available under the trade name Novamyl (product of Novo Nordisk A/S, Denmark) and is widely used in the baking industry as an anti-staling agent due to its ability to reduce retrogradation of starch. Novamyl is described in detail in International Patent Publication WO 91/04669. The maltogenic alpha-amylase Novamyl shares several characteristics with cyclodextrin glucanotransferases (CGTases), including sequence homology (Henrissat B, Bairoch A; Biochem. J., 316, 695–696 (1996)) and formation of transglycosylation products (Christophersen, C., et al., 1997, Starch, vol. 50, No. 1, 39–45).

In highly preferred embodiments, we disclose combinations comprising PS4 variant polypeptides together with Novamyl or any of its variants. Such combinations are useful for baking, food production, or for other purposes. The Novamyl may in particular comprise Novamyl 1500 MG.

Other documents describing Novamyl and its uses include Christophersen, C., Pedersen, S., and Christensen, T., (1993) Method for production of maltose an a limit dextrin, the limit dextrin, and use of the limit dextrin. Denmark, and WO 95/10627. It is further described in U.S. Pat. No. 4,598,048 and U.S. Pat. No. 4,604,355. Each of these documents is hereby incorporated by reference, and any of the Novamyl polypeptides described therein may be used in combinations with any of the PS4 variant polypeptides described here.

Variants, homologues, and mutants of Novamyl may be used for the combinations, provided they retain alpha amylase activity. For example, any of the Novamyl variants disclosed in U.S. Pat. No. 6,162,628, the entire disclosure of which is hereby incorporated by reference, may be used in combination with the PS4 variant polypeptides described here. In particular, any of the polypeptides described in that document, specifically variants of SEQ ID NO: 1 of U.S. Pat. No. 6,162,628 at any one or more positions corresponding to Q13, 116, D17, N26, N28, P29, A30, S32, Y33, G34, L35, K40, M45, P73, V74, D76 N77, D79, N86, R95, N99, 1100, H103, Q119, N120, N131, S141, T142, A148, N152, A163, H169, N171, G172, I174, N176, N187, F188, A192, Q201, N203, H220, N234, G236, Q247, K249, D261, N266, L268, R272, N275, N276, V279, N280, V281, D285, N287, F297, Q299, N305, K316, N320, L321, N327, A341, N342, A348, Q365, N371, N375, M378, G397, A381, F389, N401, A403, K425, N436, S442, N454, N468, N474, S479, A483, A486, V487, S493, T494, S495, A496, S497, A498, Q500, N507, I510, N513, K520, Q526, A555, A564, S573, N575, Q581, S583, F586, K589, N595, G618, N621, Q624, A629, F636, K645, N664 and/or T681 may be used.

Amino Acid Sequences

The invention makes use of a PS4 variant nucleic acid, and the amino acid sequences of such PS4 variant nucleic acids are encompassed by the methods and compositions described here.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The PS4 variant enzyme described here may be used in conjunction with other enzymes. Thus we further disclose a combination of enzymes wherein the combination comprises a PS4 variant polypeptide enzyme described here and another enzyme, which itself may be another PS4 variant polypeptide enzyme.

PS4 Nucleotide Sequence

As noted above, we disclose nucleotide sequences encoding the PS4 variant enzymes having the specific properties described.

The term "nucleotide sequence" or "nucleic acid sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" as used in this document includes genomic DNA, cDNA, synthetic DNA, and RNA. Preferably it means DNA, more preferably cDNA sequence coding for a PS4 variant polypeptide.

Typically, the PS4 variant nucleotide sequence is prepared using recombinant DNA techniques (i.e. recombinant DNA). However, in an alternative embodiment, the nucleotide sequence could be synthesised, in whole or in part, using chemical methods well known in the art (see Caruthers M H et al., (1980) *Nuc Acids Res Symp Ser* 215–23 and Horn T et al., (1980) *Nuc Acids Res Symp Ser* 225–232).

Preparation of Nucleic Acid Sequences

A nucleotide sequence encoding either an enzyme which has the specific properties as defined herein (e.g., a PS4 variant polypeptide) or an enzyme which is suitable for modification, such as a parent enzyme, may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. maltose), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859–1869, or the method described by Matthes et al., (1984) *EMBO J.* 3, p 801–805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487–491).

Variants/Homologues/Derivatives

We further describe the use of variants, homologues and derivatives of any amino acid sequence of an enzyme or of any nucleotide sequence encoding such an enzyme, such as a PS4 variant polypeptide or a PS4 variant nucleic acid. Unless the context dictates otherwise, the term "PS4 variant nucleic acid" should be taken to include each of the nucleic acid entities described below, and the term "PS4 variant polypeptide" should likewise be taken to include each of the polypeptide or amino acid entities described below.

Here, the term "homologue" means an entity having a certain homology with the subject amino acid sequences and the subject nucleotide sequences. Here, the term "homology" can be equated with "identity".

In the present context, a homologous sequence is taken to include an amino acid sequence which may be at least 75, 80, 85 or 90% identical, preferably at least 95, 96, 97, 98 or 99% identical to the subject sequence. Typically, the homologues will comprise the same active sites etc. as the subject amino acid sequence. Although homology can also be considered in terms of similarity (i.e. amino acid residues having similar chemical properties/functions), in the context of this document it is preferred to express homology in terms of sequence identity.

In the present context, an homologous sequence is taken to include a nucleotide sequence which may be at least 75, 80, 85 or 90% identical, preferably at least 95, 96, 97, 98 or 99% identical to a nucleotide sequence encoding a PS4 variant polypeptide enzyme (such as a PS4 variant nucleic acid). Typically, the homologues will comprise the same sequences that code for the active sites etc as the subject sequence. Although homology can also be considered in terms of similarity (i.e. amino acid residues having similar chemical properties/functions), in the context of this document it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 *Nuc. Acids Research* 12 p387). Examples of other software than can perform sequence comparisons include, but are not limited to, the BLAST package (see Ausubel et al., 1999 *Short Protocols in Molecular Biology*, 4$^{th}$ Ed—Chapter 18), FASTA (Altschul et al., 1990 *J. Mol. Biol.* 403–410) and the GENEWORKS suite of comparison tools. Both BLAST and FASTA are available for offline and online searching (see Ausubel et al., 1999, *Short Protocols in Molecular Biology*, pages 7–58 to 7–60).

However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187–8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins DG & Sharp PM (1988), Gene 73(1), 237–244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" *Comput. Appl Biosci.* 9: 745–756)(Taylor W. R. (1986) "The classification of amino acid conservation" *J. Theor. Biol.* 119; 205–218). Conservative substitutions may be made, for example according to the table below which describes a generally accepted Venn diagram grouping of amino acids.

| | Set | | Sub-set |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

We further disclose sequences comprising homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367–9371 and Horwell DC, *Trends Biotechnol*. (1995) 13(4), 132–134.

The nucleotide sequences described here, and suitable for use in the methods and compositions described here (such as PS4 variant nucleic acids) may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of this document, it is to be understood that the nucleotide sequences described herein may be modified by any method available in the art. Such modifications may be carried out in order to enhance the in vivo activity or life span of nucleotide sequences.

We further describe the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the PS4 variant sequences may be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences described here.

Variants and strain/species homologues may also be obtained using degenerate PCR which will use primers designed to target sequences within the variants and homologues encoding conserved amino acid sequences. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides (nucleotide sequences) such as the PS4 variant nucleic acids described in this document may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides.

Polynucleotides such as DNA polynucleotides and probes may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

Hybridisation

We further describe sequences that are complementary to the nucleic acid sequences of PS4 variants or sequences that are capable of hybridising either to the PS4 variant sequences or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies. Therefore, we disclose the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringent conditions (e.g. 65° C. and 0.1×SSC {1×SSC=0.15 M NaCl, 0.015 M Na$_3$citrate pH 7.0}) to the nucleotide sequences presented herein.

We further disclose nucleotide sequences that can hybridise to the nucleotide sequences of PS4 variants (including complementary sequences of those presented herein), as well as nucleotide sequences that are complementary to sequences that can hybridise to the nucleotide sequences of PS4 variants (including complementary sequences of those presented herein). We further describe polynucleotide sequences that are capable of hybridising to the nucleotide sequences presented herein under conditions of intermediate to maximal stringency.

In a preferred aspect, we disclose nucleotide sequences that can hybridise to the nucleotide sequence of a PS4 variant nucleic acid, or the complement thereof, under stringent conditions (e.g. 50° C. and 0.2×SSC). More preferably, the nucleotide sequences can hybridise to the nucleotide sequence of a PS4 variant, or the complement thereof, under high stringent conditions (e.g. 65° C. and 0.1×SSC).

Site-Directed Mutagenesis

Once an enzyme-encoding nucleotide sequence has been isolated, or a putative enzyme-encoding nucleotide sequence has been identified, it may be desirable to mutate the sequence in order to prepare an enzyme. Accordingly, a PS4 variant sequence may be prepared from a parent sequence.

Mutations may be introduced using synthetic oligonucleotides. These oligonucleotides contain nucleotide sequences flanking the desired mutation sites.

A suitable method is disclosed in Morinaga et al., (*Biotechnology* (1984) 2, p646–649). Another method of introducing mutations into enzyme-encoding nucleotide sequences is described in Nelson and Long (*Analytical Biochemistry* (1989), 180, p 147–151). A further method is described in Sarkar and Sommer (*Biotechniques* (1990), 8, p404–407—"The megaprimer method of site directed mutagenesis").

In one aspect the sequence for use in the methods and compositions described here is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1–3, Cold Spring Harbor Laboratory Press.

In one aspect the sequence for use in the methods and compositions described here is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

The nucleotide sequence for use in the methods and compositions described here may be incorporated into a recombinant replicable vector. The vector may be used to replicate and express the nucleotide sequence, in enzyme form, in and/or from a compatible host cell. Expression may be controlled using control sequences eg. regulatory sequences. The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression of PS4 Nucleic Acids and Polypeptides

The PS4 polynucleotides and nucleic acids may include DNA and RNA of both synthetic and natural origin which DNA or RNA may contain modified or unmodified deoxy- or dideoxy-nucleotides or ribonucleotides or analogs thereof. The PS4 nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides. The PS4 nucleic acid may even be codon optimised to further increase expression.

The term "synthetic", as used herein, is defined as that which is produced by in vitro chemical or enzymatic synthesis. It includes but is not limited to PS4 nucleic acids made with optimal codon usage for host organisms such as the the methylotrophic yeasts *Pichia* and *Hansenula*.

Polynucleotides, for example variant PS4 polynucleotides described here, can be incorporated into a recombinant replicable vector. The vector may be used to replicate the nucleic acid in a compatible host cell. The vector comprising the polynucleotide sequence may be transformed into a suitable host cell. Suitable hosts may include bacterial, yeast, insect and fungal cells.

The term "transformed cell" includes cells that have been transformed by use of recombinant DNA techniques. The transformation typically occurs by insertion of one or more nucleotide sequences into a cell that is to be transformed. The inserted nucleotide sequence may be a heterologous nucleotide sequence (i.e. is a sequence that is not natural to the cell that is to be transformed. In addition, or in the alternative, the inserted nucleotide sequence may be an homologous nucleotide sequence (i.e. is a sequence that is natural to the cell that is to be transformed)—so that the cell receives one or more extra copies of a nucleotide sequence already present in it.

Thus in a further embodiment, we provide a method of making PS4 variant polypeptides and polynucleotides by introducing a polynucleotide into a replicable vector, introducing the vector into a compatible host cell, and growing the host cell under conditions which bring about replication of the vector. The vector may be recovered from the host cell.

Expression Constructs

The PS4 nucleic acid may be operatively linked to transcriptional and translational regulatory elements active in a host cell of interest. The PS4 nucleic acid may also encode a fusion protein comprising signal sequences such as, for example, those derived from the glucoamylase gene from *Schwanniomyces occidentalis*, α-factor mating type gene from *Saccharomyces cerevisiae* and the TAKA-amylase from *Aspergillus oryzae*. Alternatively, the PS4 nucleic acid may encode a fusion protein comprising a membrane binding domain.

Expression Vector

The PS4 nucleic acid may be expressed at the desired levels in a host organism using an expression vector.

An expression vector comprising a PS4 nucleic acid can be any vector which is capable of expressing the gene encoding PS4 nucleic acid in the selected host organism, and the choice of vector will depend on the host cell into which it is to be introduced. Thus, the vector can be an autonomously replicating vector, i.e. a vector that exists as an episomal entity, the replication of which is independent of chromosomal replication, such as, for example, a plasmid, a bacteriophage or an episomal element, a minichromosome or an artificial chromosome. Alternatively, the vector may be one which, when introduced into a host cell, is integrated into the host cell genome and replicated together with the chromosome.

Components of the Expression Vector

The expression vector typically includes the components of a cloning vector, such as, for example, an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. Additionally, the expression vector may comprise a sequence coding for an amino acid sequence capable of targeting the PS4 variant polypeptide to a host cell organelle such as a peroxisome or to a particular host cell compartment. Such a targeting sequence includes but is not limited to the sequence SKL. In the present context, the term "expression signal" includes any of the above control sequences, repressor or activator sequences. For expression under the direction of control sequences, the nucleic acid sequence the PS4 variant polypeptide is operably linked to the control sequences in proper manner with respect to expression.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators. The control sequences may in particular comprise promoters.

Promoter

In the vector, the nucleic acid sequence encoding for the variant PS4 polypeptide is operably combined with a suitable promoter sequence. The promoter can be any DNA sequence having transcription activity in the host organism of choice and can be derived from genes that are homologous or heterologous to the host organism.

Bacterial Promoters

Examples of suitable promoters for directing the transcription of the modified nucleotide sequence, such as PS4 nucleic acids, in a bacterial host include the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes and a promoter derived from a *Lactococcus* sp.-derived promoter including the P170 promoter. When the gene encoding the PS4 variant polypeptide is expressed in a bacterial species such as *E. coli*, a suitable promoter can be selected, for example, from a bacteriophage promoter including a T7 promoter and a phage lambda promoter.

Fungal Promoters

For transcription in a fungal species, examples of useful promoters are those derived from the genes encoding the, *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase.

Yeast Promoters

Examples of suitable promoters for the expression in a yeast species include but are not limited to the Gal 1 and Gal 10 promoters of *Saccharomyces cerevisiae* and the *Pichia pastoris* AOX1 or AOX2 promoters.

Host Organisms (I) Bacterial Host Organisms

Examples of suitable bacterial host organisms are gram positive bacterial species such as Bacillaceae including *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus lautus*, *Bacillus megaterium* and *Bacillus thuringiensis*, *Streptomyces* species such as *Streptomyces murinus*, lactic acid bacterial species including *Lactococcus* spp. such as *Lactococcus lactis*, *Lactobacillus* spp. including *Lactobacillus reuteri*, *Leuconostoc* spp., *Pediococcus* spp. and *Streptococcus* spp. Alternatively, strains of a gram-negative bacterial species belonging to Enterobacteriaceae including *E. coli*, or to Pseudomonadaceae can be selected as the host organism.

(II) Yeast Host Organisms

A suitable yeast host organism can be selected from the biotechnologically relevant yeasts species such as but not limited to yeast species such as *Pichia* sp., *Hansenula* sp or *Kluyveromyces*, *Yarrowinia* species or a species of *Saccharomyces* including *Saccharomyces cerevisiae* or a species belonging to *Schizosaccharomyce* such as, for example, *S. Pombe* species.

Preferably a strain of the methylotrophic yeast species *Pichia pastoris* is used as the host organism. Preferably the host organism is a *Hansenula* species.

(III) Fungal Host Organisms

Suitable host organisms among filamentous fungi include species of *Aspergillus*, e.g. *Aspergillus niger*, *Aspergillus oryzae*, *Aspergillus tubigensis*, *Aspergillus awamori* or *Aspergillus nidulans*. Alternatively, strains of a *Fusarium* species, e.g. *Fusarium oxysporum* or of a *Rhizomucor* species such as *Rhizomucor miehei* can be used as the host organism. Other suitable strains include *Thermomyces* and *Mucor* species.

Protein Expression and Purification

Host cells comprising polynucleotides may be used to express polypeptides, such as variant PS4 polypeptides, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Polypeptides can be extracted from host cells by a variety of techniques known in the art, including enzymatic, chemical and/or osmotic lysis and physical disruption. Polypeptides may also be produced recombinantly in an in vitro cell-free system, such as the TnT™ (Promega) rabbit reticulocyte system.

PS4 Antibodies

We also provide monoclonal or polyclonal antibodies to PS4 variant polypeptides or fragments thereof. Thus, we further describe a process for the production of monoclonal or polyclonal antibodies to an variant PS4 polypeptide, fragment, homologue, variant or derivative thereof.

If polyclonal antibodies are desired, a selected mammal (e.g., mouse, rabbit, goat, horse, etc.) is immunised with an immunogenic polypeptide bearing an epitope(s) from a polypeptide. Serum from the immunised animal is collected and treated according to known procedures. If serum containing polyclonal antibodies to an epitope from a polypeptide contains antibodies to other antigens, the polyclonal antibodies can be purified by immunoaffinity chromatography. Techniques for producing and processing polyclonal antisera are known in the art. In order that such antibodies may be made, we also provide PS4 variant polypeptides or fragments thereof haptenised to another polypeptide for use as immunogens in animals or humans.

Monoclonal antibodies directed against epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes in the polypeptides can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

Antibodies, both monoclonal and polyclonal, which are directed against epitopes from polypeptides are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the agent against which protection is desired.

Techniques for raising anti-idiotype antibodies are known in the art. These anti-idiotype antibodies may also be useful in therapy. For the purposes of this document, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

In preferred embodiments, the PS4 antibody is capable of specifically binding to a particular PS4 variant polypeptide. Preferably, the antibody is capable of binding to a PS4 variant polypeptide under consideration, but not to the wild type or parent polypeptide. More preferably, the antibody is capable of binding to the PS4 variant polypeptide, but not to the parent or any other variant polypeptide. In other words, preferred antibodies are those which are capable of recognising single amino acid changes in the sequence context of PS4. Such antibodies may be made by immunisation, as described above, and screening for specific binding activity using dot blots, Western blots, etc, as known in the art.

REFERENCES

Penninga, D., van der Veen, B. A., Knegtel, R. M., van Hijum, S. A., Rozeboom, H. J., Kalk, K. H., Dijkstra, B. W., Dijkhuizen, L. (1996). The raw starch binding domain of cyclodextrin glycosyltransferase from *Bacillus circulans* strain 251. J. Biol. Chem. 271, 32777–32784.

Sambrook J, F.E.M.T. (1989). Molecular Cloning: A Laboratory Manual, 2nd Edn. Cold Spring Harbor Laboratory, Cold Spring Harbor N.Y.

Zhou, J. H., Baba, T., Takano, T., Kobayashi, S., Arai, Y. (1989). Nucleotide sequence of the maltotetraohydrolase gene from *Pseudomonas saccharophila*. FEBS Lett. 255, 37–41.

[1]. K. H. Park, Food Sci. Ind. 25 (1992) 73–82.

[2]. M. Okada and T. Nakakuki, *Oligosaccharides: production, properties and application*, in F. W. Schenck and R. E. Hebeda (Eds.), *Starch hydrolysis products worldwide technology, production and application*, VCH Publishers, New York, 1992, pp 335–366.

[3]. W. M. Fogarty, *Microbial amylases*, in W. M. Fogarty (Ed.), *Microbial enzymes and biotechnology*, Applied Science, London, 1983, pp. 1–92.

[4]. W. M. Fogarty and C. T. Kelly, *Starch-degrading enzymes of microbial origin*, in M. J. Bull (Ed.), *Progress in industrial microbiology*, Vol. 15, Elsevier Scientific 1979, pp. 87–150.

[5]. K. Kainuma, S. Kobayashi, T. Ito, and S. Suzuki, FEBS Letters, 26 (1972) 281–285.

[6]. N. Monma, T. Nakakuki, and K. Kainuma, Agric. Biol. Chem., 47 (1983) 1769–1774.

[7]. J. F. Kennedy and C. A. White, Starch/Stärke 31 (1979) 93–99.

[8]. Y. Takasaki, Agric. Biol. Chem. 46 (1982) 1539–1547.

[9]. H. Taniguchi, C. M. Jae, N. Yoshigi, and Y. Maruyama, Agric. Biol. Chem. 47 (1983) 511–519.

[10]. H. Taniguchi, *Maltohexaose-producing amylase of Bacillus circulans F-2* in R. B. Friedman (Ed.) *Biotechnology of amylodextrin oligosaccharides. A CS Symp. Ser.* 458. American Chemical Society, Washington D.C., 1991, pp 111–124.

[11]. F. Bealin-Kelly, C. T. Kelly, and W. M. Fogarty, Biochem. Soc. Trans., 18 (1990) 310–311.

[12]. W. M. Fogarty, F. Bealin-Kelly, C. T. Kelly, and E. M. Doyle, Appl. Microbiol. Biotechnol., 36 (1991) 184489.

[13]. N. Saito, Archives. Biochem. Biophys., 155 (1973) 290–298.

[14]. H. Okemoto, S. Kobayashi, M. Monma, H. Hashimoto, K. Hara, and K. Kainuma, Appl. Microbiol. Biotechnol., 25 (1986) 137–142.

[15]. O. Shida, T. Takano, H. Takagi, K. Kadowaki, and S. Kobayashi, Biosci., Biotechnol., Biochem. 56 (1992) 76–80.

[16]. (There is no ref. [16])

[17]. Y. Sakano, Y. Kashiwagi, and T. Kobayashi, Agric. Biol. Chem., 46 (1982) 639–646.

[18]. Y. Takasaki, H. Shinohara, M. Tsuruhisa, S. Hayashi, K. Imada, Agric. Biol. Chem. 55 (1991) 1715–1720.

[19]. W. M. Fogarty, C. T. Kelly, A. C. Bourke, and E. M. Doyle, Biotechnol. Lett. 16 (1994) 473–478.

[20]. K. Wako, S. Hashimoto, S. Kubomura, A. Yokota, K. Aikawa, and J. Kamaeda, J. Jap. Soc. Starch. Sci 26 (1979) 175–181.

[21]. Y. Takasaki, Agric. Biol. Chem. 49 (1985) 1091–1097.

[22]. (There is no ref. [22])

[23]. T. Hayashi, T. Akiba, and K. Horikoshi, Appl. Microbiol. Biotechnol. 28 (1988b) 281–285.

[24]. G. Schmid, A. Candussio, and A. Bock, U.S. Pat. No. 5,304,723 (1994).

[25] M. A. Mc Tigue, C. T. Kelly, E. M. Doyle, and W. M. Fogarty, Enzyme Microb. Technol., 17 (1995) 570–573.

[26]. T. U. Kim, B. G. Gu, J. Y. Jeong, S. M. Byun, and Y. C. Shin, Appl. Environm. Microbiol. 61 (1995) 3105–3112.

EXAMPLES

Example 1

Cloning of PS4

*Pseudomonas sacharophila* is grown overnight on LB media and chromosomal DNA is isolated by standard methods (Sambrook J, 1989). A 2190 bp fragment containing the PS4 openreading frame (Zhou et al., 1989) is amplified from *P. sacharophila* chromosomal DNA by PCR using the primers P1 and P2 (see Table 1). The resulting fragment is used as a template in a nested PCR with primers P3 and P4, amplifying the openreading frame of PS4 without its signal sequence and introducing a NcoI site at the 5' end of the gene and a BamHI site at the 3'end. Together with the NcoI site a codon for a N-terminal Methionine is introduced, allowing for intracellular expression of PS4. The 1605 bp fragment is cloned into pCRBLUNT TOPO (Invitrogen) and the integrity of the construct analysed by sequencing.

The *E. coli Bacillus* shuttle vector pDP66K (Penninga et al., 1996) is modified to allow for expression of the PS4 under control of the P32 promoter and the ctgase signal sequence. The resulting plasmid, pCSmta (see FIG. 1) is transformed into *B. subtilis*.

A second expression construct is made in which the starch binding domain of PS4 is removed. In a PCR with primers P3 and P6 (Table 1) on pCSmta, a truncated version of the mta gene is generated. The full length mta gene in pCSmta is exchanged with the truncated version which resulted in the plasmid pCSmta-SBD (FIG. 1)

Example 2

Site Directed Mutagenesis

Mutations are introduced into the mta gene by 2 methods. Either by a 2 step PCR based method, or by a Quick Exchange method (QE). For convenience the mta gene is split up in 3 parts; a PvuI-FspI fragment, a FspI-PstI fragment and a PstI-AspI fragment, further on referred to as fragment 1, 2 and 3 respectively.

In the 2 step PCR based method, mutations are introduced using Pfu DNA polymerase (Stratagene). A first PCR is carried out with a mutagenesis primer (Table 2) for the coding strand plus a primer downstream on the lower strand (either 2R or 3R Table 1). The reaction product is used as a primer in a second PCR together with a primer upstream on the coding strand. The product of the last reaction is cloned into pCRBLUNT topo (Invitrogen) and after sequencing the fragment is exchanged with the corresponding fragment in pCSmta.

Using the Quick Exchange method (Stratagene), mutations are introduced using two complementary primers in a PCR on a plasmid containing the mta gene, or part of the mta gene.

Figure 2:
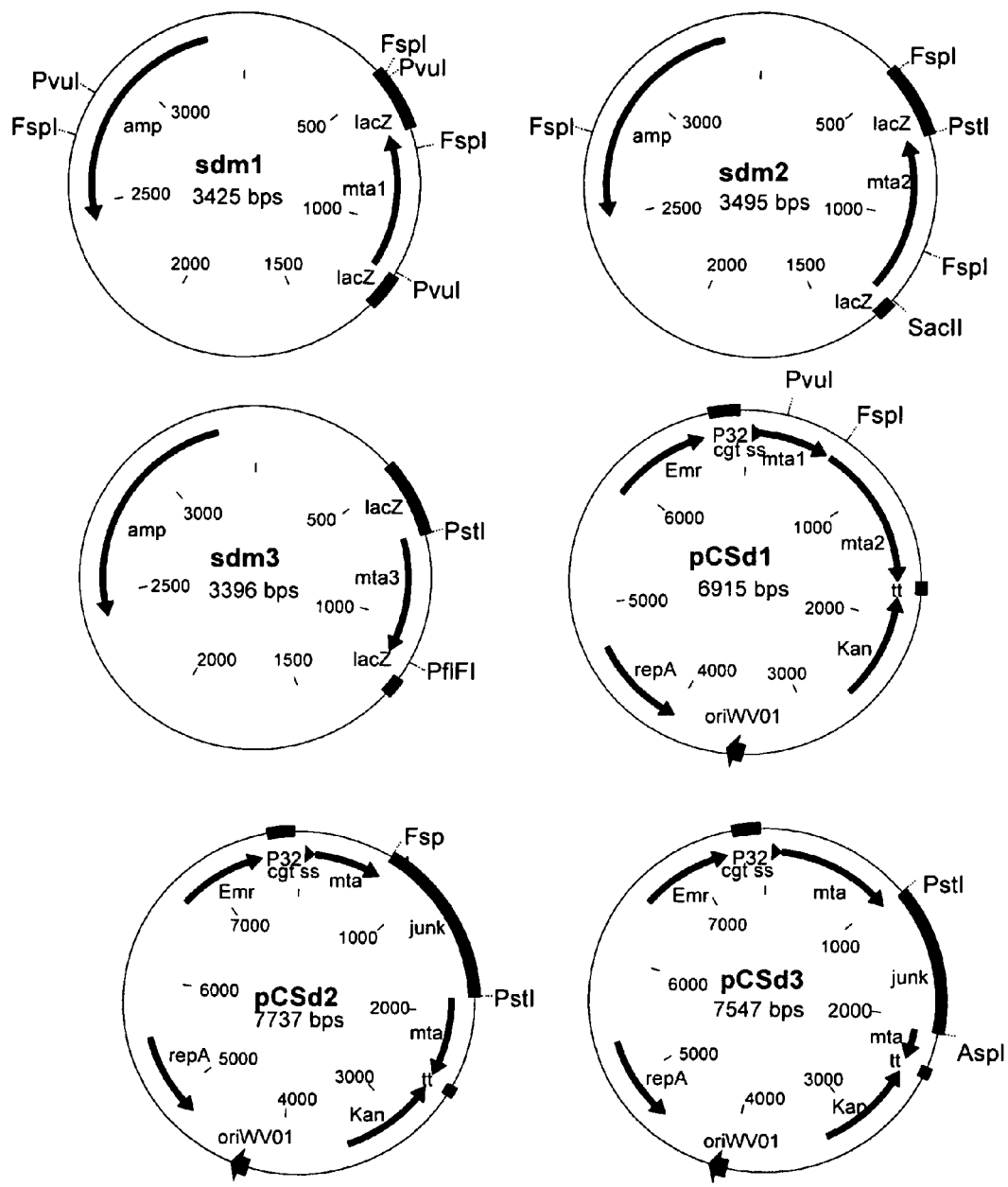
FIG. 2. Plasmids used in the Quick Exchange method. Mutations were made using one of the SDM vectors, and after confirmation of the desired mutation by sequencing, the fragment was placed back into the corresponding pCSΔ vector. Restriction sites used for exchanging the fragments are indicated.

For this purpose a convenient set of plasmids is constructed, comprising of 3 SDM plasmids and 3 pCSΔ plasmids (FIG. 2). The SDM plasmids each bear 1 of the fragments of the mta gene as mentioned above, in which the desired mutation is introduced by QE. After verification by sequencing, the fragments are cloned into the corresponding recipient pCSΔ plasmid. The pCSΔ plamids are inactive derivatives from pCSmta. Activity is restored by cloning the corresponding fragment from the SDM plasmid, enabling easy screening.

TABLE 1

Primers used in cloning the mta gene, and standard primers used in construction of site directed mutants with the 2 step PCR method.

| Primer | Primer sequence | Introduced site |
|---|---|---|
| P1 | 5'-ATG ACG AGG TCC TTG TTT TTC (SEQ ID NO: 22) | |
| P2 | 5'-CGC TAG TCG TCC ATG TCG (SEQ ID NO: 23) | |
| P3 | 5'-G<u>CC ATG G</u>AT CAG GCC GGC AAG AGC CCG (SEQ ID NO: 24) | NcoI |
| P4 | 5'-T<u>GG ATC C</u>TC AGA ACG AGC CGC TGG T (SEQ ID NO: 25) | BamHI |
| P6 | 5'-<u>GAA TTC</u> AGC CGC CGT CAT TCC CGC C (SEQ ID NO: 26) | EcoRI |
| 2L | 5'-AGA TTT ACG GCA TGT TTC GC (SEQ ID NO: 27) | |
| 2R | 5'-TAG CCG CTA TGG AAG CTG AT (SEQ ID NO: 28) | |
| 3L | 5'-TGA CCT TCG TCG ACA ACC AC (SEQ ID NO: 29) | |
| 3R | 5'-GAT AGC TGC TGG TGA CGG TC (SEQ ID NO: 30) | |

TABLE 2

Primers used to introduce site directed mutations in mta. If used in the Quick Exchange method, a complementary lower-strand primer is used in combination with the mentioned primer. The template on which the PCR is run is indicated and the used method. Mutations are indicated in bold, and introduced or removed restriction sites underlined and mentioned.

| Mutant | Template | Method | Primer (upper) | Introduced site |
|---|---|---|---|---|
| G69P | SDM1 | QE | AGC TGG ACC GA<u>C CCG GGC</u> AAG TCC GGC (SEQ ID NO: 31) | +XmaI |
| 103P | SDM1 | QE | GCC GGC G<u>CA CTC CCT G</u>GC GCC GGG GTG (SEQ ID NO: 32) | −DraIII |

TABLE 2-continued

Primers used to introduce site directed mutations in mta. If used in the Quick Exchange method, a complementary lower-strand primer is used in combination with the mentioned primer. The template on which the PCR is run is indicated and the used method. Mutations are indicated in bold, and introduced or removed restriction sites underlined and mentioned.

| Mutant | Template | Method | Primer (upper) | Introduced site |
|---|---|---|---|---|
| G121P | SDM1 | QE | CAC ATG AAC CGC CCG TAC CCG GAC AAG (SEQ ID NO: 33) | −SacII |
| G132P | SDM1 | QE | CAA CCT GCC GGC CCC GCA GGG CTT CTG G (SEQ ID NO: 34) | −FseI |
| A141P | SDM1 | QE | CGC AAC GAC TGC CCG GAT CCG GGC AAC (SEQ ID NO: 35) | +BamHI |
| S161P | SDM1 | QE | ATC GGC GGC GAG CCA GAT CTG AAC ACC (SEQ ID NO: 36) | +BglII |
| A199P | SDM2 | QE | GTT CGC GGC TAT CCG CCC GAG CGG GTC (SEQ ID NO: 37) | — |
| S213P | SDM2 | QE | GAC AGC GCC GAC CCA AGC TTC TGC GTT (SEQ ID NO: 38) | — |
| 223A | SDM2 | QE | GAG CTG TGG AAA GCC CCT TCT GAA TAT C (SEQ ID NO: 39) | — |
| 268P | pCSmta | 2PCR | AAC GGC TCG GTC CCG GAC TGG AAG CAT (SEQ ID NO: 40) | — |
| G313P | pCSmta | 2PCR | GCG CTG CAG GAC CCG CTG ATC CGC CAG (SEQ ID NO: 41) | +EcoO109 |
| 342P | pCSmta | 2PCR | GAC TGG GGC TAC CCG GAC TTC ATC CGC (SEQ ID NO: 42) | — |
| 367P | SDM3 | QE | GCG ATA AGC TTC CAT CCG GGC TAC AGC (SEQ ID NO: 43) | +HinDIII |
| 399P | SDM3 | QE | GGC CAG GTT GCC CCG GGA AGC TTC AGC (SEQ ID NO: 44) | +HinDIII |
| 400P | SDM3 | QE | CAG GTT GCC AGC CCG AGC TTC AGC GAG (SEQ ID NO: 45) | +AvaI |

TABLE 3

Constructed mutants. In most of the site directed mutants a restriction site is added, allowing for quick identification. Site directed mutants are either created by a Quick Exchange method (QE) or by a 2 PCR based method as described above.

| Mutant | Identification | 2 PCR/QE | cloned in: | Location |
|---|---|---|---|---|
| G69P | +XmaI | QE | pCSΔ1 | 1 |
| G103P | −DraIII | QE | pCS-mta | 1 |
| G121P | −SacII | QE | pCS-mta | 1 |
| G132P | −FseI | QE | pCS-mta | 1 |
| A141P | +BamHI | QE | pCS-mta | 1 |
| S161P | +BglII | QE | pCSΔ1 | 1 |
| A199P | — | QE | pCSΔ2 | 2 |
| S213P | +HinDIII | QE | pCSΔ2 | 2 |
| G223A | — | QE | pCSΔ2 | 2 |
| A268P | — | 2PCR | pCSΔ2 | 2 |
| G313P | +EcoO109 | 2PCR | pCSΔ3 | 3 |
| G342P | — | 2PCR | pCSΔ3 | 3 |
| S367P | +HinDIII | QE | pCSΔ3 | 3 |
| S399P | +HinDIII | QE | pCSΔ3 | 3 |
| G400P | +AvaI | QE | pCSΔ3 | 3 |

TABLE 4

Features of the SDM and pCSΔ plasmids

| Plasmid | Features/construction |
|---|---|
| SDM1 | pBlueSK + 480 bp SalI-StuI fragment mta |
| SDM2 | pBlueSK + 572 bp SacII-PstI fragment mta |
| SDM3 | pBlueSK + 471 bp SalI-StuI fragment mta |

TABLE 4-continued

Features of the SDM and pCSΔ plasmids

| Plasmid | Features/construction |
|---|---|
| pCSΔ1 | FseI site filled in with Klenow ----> frameshift in mta |
| pCSΔ2 | FspI-PstI fragment of mta replaced with 'junk-DNA' |
| pCSΔ3 | PstI-AspI fragment of mta replaced with 'junk-DNA' |

Example 3

Transformation into *Bacillus subtilis* (Protoplast Transformation)

*Bacillus subtilis* (strain DB104A; Smith et al. 1988; Gene 70, 351–361) is transformed with the mutated pCS-plasmids according to the following protocol.

A. Media for Protoplasting and Transformation

| | |
|---|---|
| 2 × SMM | per liter: 342 g sucrose (1 M); 4.72 g sodium maleate (0.04 M); 8:12 g MgCl$_2$, 6H$_2$0 (0.04 M); pH 6.5 with concentrated NAOH. Distribute in 50-ml portions and autoclave for 10 min. |
| 4 × YT (1/2 NaCl) | 2 g Yeast extract + 3.2 g Tryptone + 0.5 g NaCl per 100 ml. |
| SMMP | mix equal volumes of 2 × SMM and 4 × YT. |
| PEG | 10 g polyethyleneglycol 6000 (BDH) or 8000 (Sigma) in 25 ml 1 × SMM (autoclave for 10 min.). |

B. Media for Plating/Regeneration

| | |
|---|---|
| agar | 4% Difco minimal agar. Autoclave for 15 min. |
| sodium succinate | 270 g/l (1 M), pH 7.3 with HCl. Autoclave for 15 min. |
| phosphate buffer | 3.5 g K$_2$HPO$_4$ + 1.5 g KH$_2$PO$_4$ per 100 ml. Autoclave for 15 min. |
| MgCl$_2$ | 20.3 g MgCl$_2$, 6H$_2$O per 100 ml (1 M). |
| casamino acids | 5% (w/v) solution. Autoclave for 15 min. |
| yeast extract | 10 g per 100 ml, autoclave for 15 min. |
| glucose | 20% (w/v) solution. Autoclave for 10 min. |
| DM3 regeneration medium: | mix at 60 C (waterbath; 500-ml bottle): 250 ml sodium succinate 50 ml casamino acids 25 ml yeast extract 50 ml phosphate buffer 15 ml glucose 10 ml MgCl$_2$ 100 ml molten agar Add appropriate antibiotics: chloramphenicol and tetracycline, 5 ug/ml; erythromycin, 1 ug/ml. Selection on kanamycin is problematic in DM3 medium: concentrations of 250 ug/ml may be required. |

C. Preparation of Protoplasts

1. Use detergent-free plastic or glassware throughout.
2. Inoculate 10 ml of 2×YT medium in a 100-ml flask from a single colony. Grow an overnight culture at 25–30 C in a shaker (200 rev/min).
3. Dilute the overnight culture 20 fold into 100 ml of fresh 2×YT medium (250-ml flask) and grow until OD$_{600}$=0.4–0.5 (approx. 2 h) at 37 C in a shaker (200–250 rev/min).
4. Harvest the cells by centrifugation (9000 g, 20 min, 4 C).
5. Remove the supernatant with pipette and resuspend the cells in 5 ml of SMMP+5 mg lysozyme, sterile filtered.
6. Incubate at 37 C in a waterbath shaker (100 rev/min).

After 30 min and thereafter at 15 min intervals, examine 25 ul samples by microscopy. Continue incubation until 99% of the cells are protoplasted (globular appearance).

Harvest the protoplasts by centrifugation (4000 g, 20 min, RT) and pipet off the supernatant. Resuspend the pellet gently in 1–2 ml of SMMP.

The protoplasts are now ready for use. (Portions (e.g. 0.15 ml) can be frozen at −80 C for future use (glycerol addition is not required). Although this may result in some reduction of transformability, 106 transformants per ug of DNA can be obtained with frozen protoplasts).

D. Transformation

1. Transfer 450 ul of PEG to a microtube.
2. Mix 1–10 ul of DNA (0.2 ug) with 150 ul of protoplasts and add the mixture to the microtube with PEG. Mix immediately, but gently.
3. Leave for 2 min at RT, and then add 1.5 ml of SMMP and mix.
4. Harvest protoplasts by microfuging (10 min, 13.000 rev/min (10–12.000 g)) and pour off the supernatant. Remove the remaining droplets with a tissue.

Add 300 ul of SMMP (do not vortex) and incubate for 60–90 min at 37 C in a waterbath shaker (100 rev/min) to allow for expression of antibiotic resistance markers. (The protoplasts become sufficiently resuspended through the shaking action of the waterbath.)

Make appropriate dilutions in 1×SSM and plate 0.1 ml on DM3 plates

Example 4

Fermentation of PS4 Variants in Shake Flasks

The shake flask substrate is prepared as follows:

| Ingredient | % (w/v) |
|---|---|
| Water | — |
| Yeast extract | 2 |
| Soy Flour | 2 |
| NaCl | 0.5 |
| Dipotassium phosphate | 0.5 |
| Antifoam agent | 0.05 |

The substrate is adjusted to pH 6.8 with 4N sulfuric acid or sodium hydroxide before autoclaving. 100 ml of substrate is placed in a 500 ml flask with one baffle and autoclaved for 30 minutes. Subsequently, 6 ml of sterile dextrose syrup is added.

The dextrose syrup is prepared by mixing one volume of 50% w/v dextrose with one volume of water followed by autoclaving for 20 minutes.

The shake flask are inoculated with the variants and incubated for 24 hours at 35° C./180 rpm in an incubator. After incubation cells are separate from broth by centrifugation (10.000×g in 10 minutes) and finally, the supernatant is made cell free by microfiltration at 0,2 μm.

The cell free supernatant is used for assays and application tests.

Example 5

Exo-amylase Assay

One unit is defined as activity degrading 1 umol per 1 min. of PNP-coupled maltopentaose so that 1 umol PNP per 1 min. can be released by excess a-glucosidase in the assay mix.

The assay mix contains 50 ul 50 mM Na-citrate, 5 mM $CaCl_2$, pH 6,5 with 25 ul enzyme sample and 25 ul Betamyl substrate (Glc5-PNP and a-glucosidase) from Megazyme, Ireland (1 vial dissolved in 10 ml water).

The assay mix is incubated for 30 min. at 40 C and then stopped by adding 150 ul 4% Tris.

Absorbance at 420 nm is measured using an ELISA-reader and the activity is calculate based on Activity=A420*d*0,0351 U/ml enzyme sample.

Example 6

Half-life Determination

Definition t½ is the time (in minutes) during which half the enzyme activity is inactivated under defined heat conditions.

Principle: In order to determine the half life of the enzyme, the sample is heated for 1–10 minutes at 60° C. or higher. The half life value will then be calculated by measuring the residual amylase activity.

Reagents: Buffer: 50 mM Citric acid, 5 mM $CaCl_2$, pH 6.5. Dissolve 10.5 g citric acid in $dH_2O$, add 5 ml 1M $CaCl_2$ and adjust pH to 6.5 with 2M NaOH. Substrate: Exo-amylase reaction mix according to assay procedure.

Equipment: Eppendorf Heat Incubator (Termomixer comfort), Mutipipette, ELISA reader.

Temperature: 60° C. or higher up to 90° C.

Procedure: In an Eppendorf vial, 1000 µl buffer is preheated for at least 10 minutes at 60° C. or higher. The heat treatment of the sample is started addition of 100 µl of the sample to the preheated buffer under continuous mixing (800 rpm). After 0, 2, 4, 6, 8 and 9 minutes of incubation, the treatment is stopped by transferring 45 µl of the sample to 1000 µl of the buffer equilibrated at 20° C. and incubating for one minute at 1500 rpm and at 20° C. The residual activity is measured with the exo-amylase assay.

Calculation: Calculation of t½ is based on the slope of log 10 (the base-10 logarithm) of the residual amylase activity versus the incubation time. t½ is calculated as Slope/0.301=t½

Example 7

Baking Tests

Preparation of Doughs

The doughs are made in the Farinograph at 30.0° C.

10.00 g reformed flour is weighed out and added in the Farinograph; after 1 min. the reference/sample (reference=buffer or water, sample=enzyme+buffer or water) is added with a sterile pipette through the holes of the kneading vat. After 30 sec. the flour is scraped off the edges—also through the holes of the kneading vat. The sample is kneaded for 7 min.

A test with buffer or water is performed on the Farinograph before the final reference is run. FU should be 400 on the reference, if it is not, this should be adjusted with, for example, the quantity of liquid.

The reference/sample is removed with a spatula and placed in the hand (with a disposable glove on it), before it is filled into small glass tubes (of approx. 4.5 cm's length) that are put in NMR tubes and corked up. 7 tubes per dough are made.

The Farinograph is cleaned with demineralised water and wiped with Kimwipes between each test.

When all the samples have been run, the tubes are placed in a (programmable) water bath at 33° C. (without corks) for 25 min. and hereafter the water bath is set to profile 4 or 5.

Profile 4: 5 min. at 33° C., then the water bath is heated to 98° C. over 56 min. (1.1° C. per minute) and kept at 96° C. for 5 min. This is to make sure that the 95° C. are reached. Method 1-M1.

After 7 days of storage at 20.0° C. in a thermo cupboard 10–20 mg samples of crumb weighed out and placed in 40 µl aluminium standard DSC capsules. 10 capsules are prepared per treatment and kept at 20° C.

The capsules are used for Differential Scanning Calorimetry on a Metler Toledo DSC (XX). As parameters are used a heating cycle of 20–95° C. with 10° C. per minute. Gas/flow: $N_2$/80 ml per minute.

When all the capsules have been tested, the results are peaked and the following parameters are calculated: Integral: mJ; Normalized: Jg^-1, Onset: ° C.

Example 8

Thermostability Results

When analysed for thermostability the following half-lifes are determined for the variants and wild type PS4 as shown in Table 5.

TABLE 5

Half-lifes at 60° C. determined for wild type PS4 and variants containing the listed mutations

| | Mutation | t½ (60° C.) |
|---|---|---|
| 1 | Wild type PS4 | 2.1 |
| 2 | G69P | 2.5 |
| 3 | G103P | 2.3 |
| 4 | G121P | 1.8 |
| 5 | G132P | nd |
| 6 | A141P | 8.0 |
| 7 | S161P | nd |
| 8 | A199P | 1.3 |
| 9 | S213P | 2.2 |
| 10 | G223A | 3.2 |
| 11 | A268P | 3.4 |
| 12 | G313P | 2.5 |
| 13 | G342P | nd |
| 14 | S367P | 1.9 |
| 15 | S399P | 4.4 |
| 16 | G400P | 2.5 |

Example 9

Antistaling Effects

Figure 3:
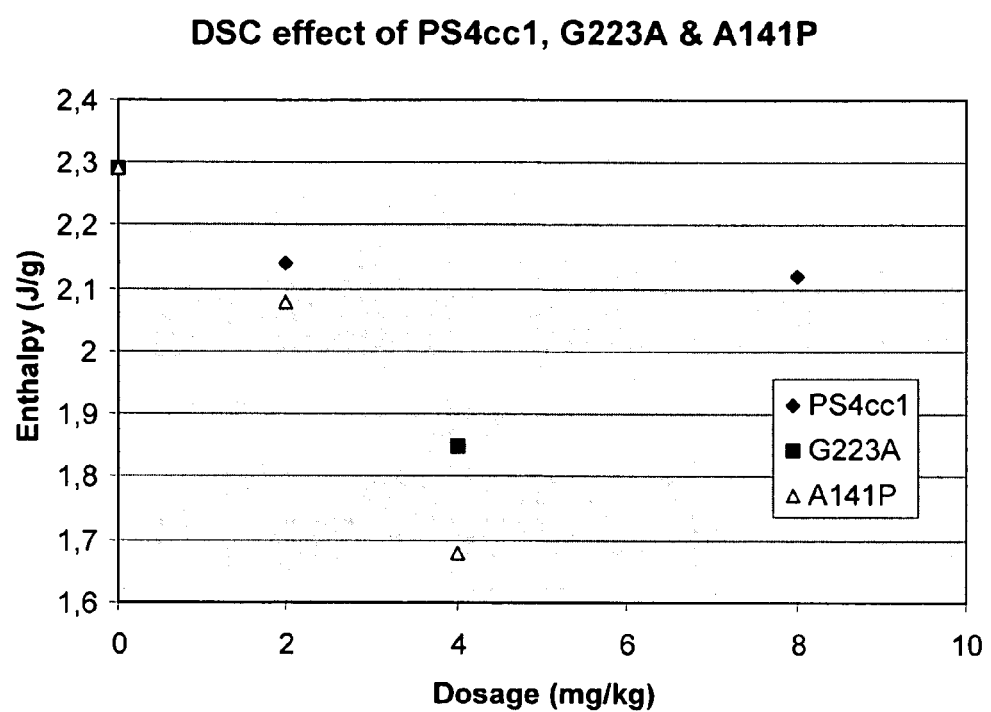
FIG. 3. Antistaling effect of PS4 variants with mutations A141P and G223A in comparison with wild type PS4 (PS4 cc1) measured by Differential Scanning Calorimetry (DSC).

Model bread crumbs are prepared and measured according to Example 7. As 2060 shown in FIG. 3, PS4 variants with mutations A141P and G223A show a reduction of the amylopectin retrogradation after baking as measured by Differential Scanning Calorimetry in comparison to wild type PS4 (PS4 cc1). The variant A141P with increased thermostability also shows an increased dosage effect in contrast to wild type PS4 (PS4 cc1).

Example 10

Control of volume of Danish Rolls

Danish Rolls are prepared from a dough based on 2000 g Danish reform flour (from Cerealia), 120 g compressed yeast, 32 g salt, and 32 g sucrose. Water is added to the dough according to prior water optimisation.

The dough is mixed on a Diosna mixer (2 min. at low speed and 5 min. at high speed). The dough temperature after mixing is kept at 26° C. 1350 g dough is scaled and rested for 10 min. in a heating cabinet at 30° C. The rolls are moulded on a Fortuna molder and proofed for 45 min. at 34° C. and at 85% relative humidity. Subsequently the rolls are baked in a Bago 2 oven for 18 min. at 250° C. with steam in the first 13 seconds. After baking the rolls are cooled for 25 min. before weighing and measuring of volume.

The rolls are evaluated regarding crust appearance, crumb homogeneity, caping of the crust, ausbund and specific volume (measuring the volume with the rape seed displacement method).

Based on these criteria it is found that the PS4 variant A141P (dosed at 0.1–0.2 mg per kg of flour) increases the specific volume and improve the quality parameters of Danish rolls. Thus PS4 variants are able to control the volume of baked products.

REFERENCES

Each of the applications and patents mentioned in this document, and each document cited or referenced in each of the above applications and patents, including during the prosecution of each of the applications and patents ("application cited documents"), and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

---

The invention claimed is:

1. A PS4 variant polypeptide derivable from a parent polypeptide, the parent polypeptide having non-maltogenic exoamylase activity, which PS4 variant polypeptide comprises a proline substitution at position 141 with reference to the position numbering of a *Pseudomonas saccharophilia* exoamylase sequence shown as SEQ ID NO: 1, in which the PS4 variant polypeptide has at least 95% homology to SEQ ID NO: 1 and non-maltogenic exoamylase activity and a higher thermostability compared to the parent polypeptide when tested under the same conditions.

2. A PS4 variant polypeptide according to claim 1, in which the parent polypeptide comprises a glucan 1,4-alpha-maltotetrahydrolase (EC 3.2.1.60).

3. A PS4 variant polypeptide according to claim 2, in which the parent polypeptide is a non-maltogenic exoamylase of *Pseudomonas saccharophilia* or *Pseudomonas stutzeri*.

4. A PS4 variant polypeptide according to claim 3, in which the parent polypeptide is a non-maltogenic exoamylase from *Pseudomonas saccharophilia* having a sequence shown as SEQ ID NO: 1.

5. A PS4 variant polypeptide according to claim 1, in which the thermostability is measured by establishing a half life ($t_{1/2}$), at 60 degrees C.

6. A PS4 variant polypeptide according to claim 1, which has a higher pH stability compared to the parent polypeptide when tested under the same conditions, wherein the pH is between pH5 to pH10.5.

7. A PS4 variant polypeptide according to claim 6, which has 10% or more pH stability compared to the parent polypeptide, wherein the pH is between pH5 to pH10.5.

8. A PS4 variant polypeptide according to claim 1, which further comprises an alanine substitution G223A.

9. A PS4 variant polypeptide according to claim 1, which comprises a sequence PSac-A141P (SEQ ID NO: 3.

10. A PS4 variant polypeptide derivable from a parent polypeptide, the parent polypeptide having non-maltogenic exoamylase activity, which PS4 variant polypeptide comprises a proline substitution at position 141, or an alanine substitution at position 223, or both, with reference to the position numbering of a *Pseudomonas saccharophilia* exoamylase sequence shown as SEQ ID NO: 1, in which the PS4 variant polypeptide has at least 95% homology to SEQ ID NO:1 and non-maltogenic exoamylase activity and a higher thermostability compared to the parent polypeptide when tested under the same conditions.

11. A polypeptide sequence comprising a sequence of a non-maltogenic exoamylase which has been mutated to include a proline substitution at an amino acid position 141 or an alanine substitution at position 223, or both, with reference to a *Pseudomonas saccharophilia* exoamylase sequence shown as SEQ ID NO: 1.

12. A PS4 variant polypeptide according to claim 5, in which the half life ($t_{1/2}$) at 60 degrees C. is increased by 15% or more relative to the parent polypeptide.

13. A PS4 variant polypeptide according to claim 5, in which the half life ($t_{1/2}$) at 60 degrees C. is increased by 50% or more relative to the parent polypeptide.

14. A PS4 variant polypeptide according to claim 5, in which the half life ($t_{1/2}$) at 60 degrees C. is increased by 100% or more relative to the parent polypeptide.

15. A PS4 variant polypeptide according to claim 1, which has a higher activity compared to the parent polypeptide.

16. A PS4 variant polypeptide according to claim 15, in which the activity is tested using a waxy maize starch incubation test.

17. A PS4 variant polypeptide according to claim 6, which has 20% or more pH stability compared to the parent polypeptide.

18. A PS4 variant polypeptide according to claim 6, which has 50% or more pH stability compared to the parent polypeptide.

19. A PS4 variant polypeptide according to claim 1, in which the polypeptide is obtainable by altering the sequence of a parent polypeptide having non-maltogenic exoamylase activity, by introducing a proline substitution at position 141 with reference to the position numbering of a *Pseudomonas saccharophilia* exoamylase sequence shown as SEQ ID NO: 1 such that the polypeptide has a higher thermostability compared to the parent polypeptide when tested under the same conditions.

20. A polypeptide according to claim 19, which is obtainable by altering the sequence of a nucleic acid which encodes the parent polypeptide.

21. A PS4 variant polypeptide derivable from a parent polypeptide, the parent polypeptide being a non-maltogenic exoamylase from *Pseudomonas saccharophilia*, the variant having a sequence shown as SEQ ID NO: 1 and non-maltogenic exoamylase activity and comprising a proline substitution at position 141, or a polypeptide which has at least 95% similarity thereto, non-maltogenic exoamylase activity and a proline residue at position 141.

22. A polypeptide obtainable by altering the sequence of a non-maltogenic exoamylase from *Pseudomonas saccharophilia* having a sequence shown as SEQ ID NO: 1, or a polypeptide which has at least 95% similarity thereto, by introducing a proline substitution at position 141.

23. A polypeptide according to claim 22, which is obtainable by altering the sequence of a nucleic acid which encodes the non-maltogenic exoamylase from *Pseudomonas saccharophilia*.

24. A combination of a PS4 variant polypeptide according to any preceding claim, together with Novamyl, or a variant, homologue, or mutants thereof which has alpha amylase activity, or a composition comprising such.

* * * * *

SEQUENCE LISTING

<160> NUMBER OF SEQ ID NOS: 45

<210> SEQ ID NO 1
<211> LENGTH: 530
<212> TYPE: PRT
<213> ORGANISM: Pseudomonas saccharophila

<400> SEQUENCE: 1

```
Asp Gln Ala Gly Lys Ser Pro Ala Gly Val Arg Tyr His Gly Gly Asp
 1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Gly Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175
```

```
Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
        515                 520                 525

Ser Phe
    530

<210> SEQ ID NO 2
<211> LENGTH: 530
<212> TYPE: PRT
<213> ORGANISM: Pseudomonas saccharophila

<400> SEQUENCE: 2

Asp Gln Ala Gly Lys Ser Pro Ala Gly Val Arg Tyr His Gly Gly Asp
1               5                   10                  15
```

-continued

```
Glu Ile Ile Leu Gln Gly Phe His Trp Asn Val Val Arg Glu Ala Pro
         20                  25                  30
Asn Asp Trp Tyr Asn Ile Leu Arg Gln Gln Ala Ser Thr Ile Ala Ala
         35                  40                  45
Asp Gly Phe Ser Ala Ile Trp Met Pro Val Pro Trp Arg Asp Phe Ser
 50                  55                  60
Ser Trp Thr Asp Pro Gly Lys Ser Gly Gly Glu Gly Tyr Phe Trp
 65                  70                  75                  80
His Asp Phe Asn Lys Asn Gly Arg Tyr Gly Ser Asp Ala Gln Leu Arg
                 85                  90                  95
Gln Ala Gly Ala Leu Gly Gly Ala Gly Val Lys Val Leu Tyr Asp
                100                 105                 110
Val Val Pro Asn His Met Asn Arg Gly Tyr Pro Asp Lys Glu Ile Asn
                115                 120                 125
Leu Pro Ala Gly Gln Gly Phe Trp Arg Asn Asp Cys Ala Asp Pro Gly
 130                 135                 140
Asn Tyr Pro Asn Asp Cys Asp Asp Gly Asp Arg Phe Ile Gly Gly Glu
145                 150                 155                 160
Ser Asp Leu Asn Thr Gly His Pro Gln Ile Tyr Gly Met Phe Arg Asp
                165                 170                 175
Glu Leu Ala Asn Leu Arg Ser Gly Tyr Gly Ala Gly Gly Phe Arg Phe
                180                 185                 190
Asp Phe Val Arg Gly Tyr Ala Pro Glu Arg Val Asp Ser Trp Met Ser
                195                 200                 205
Asp Ser Ala Asp Ser Ser Phe Cys Val Gly Glu Leu Trp Lys Gly Pro
 210                 215                 220
Ser Glu Tyr Pro Ser Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Val Ala Asp Trp Lys His
                260                 265                 270
Gly Leu Asn Gly Asn Pro Asp Pro Arg Trp Arg Glu Val Ala Val Thr
                275                 280                 285
Phe Val Asp Asn His Asp Thr Gly Tyr Ser Pro Gly Gln Asn Gly Gly
                290                 295                 300
Gln His His Trp Ala Leu Gln Asp Gly Leu Ile Arg Gln Ala Tyr Ala
305                 310                 315                 320
Tyr Ile Leu Thr Ser Pro Gly Thr Pro Val Val Tyr Trp Ser His Met
                325                 330                 335
Tyr Asp Trp Gly Tyr Gly Asp Phe Ile Arg Gln Leu Ile Gln Val Arg
                340                 345                 350
Arg Thr Ala Gly Val Arg Ala Asp Ser Ala Ile Ser Phe His Ser Gly
                355                 360                 365
Tyr Ser Gly Leu Val Ala Thr Val Ser Gly Ser Gln Gln Thr Leu Val
                370                 375                 380
Val Ala Leu Asn Ser Asp Leu Ala Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Asn Asp Gly Gly Glu Gly Gly
                420                 425                 430
```

-continued

```
Leu Val Asn Val Asn Phe Arg Cys Asp Asn Gly Val Thr Gln Met Gly
            435                 440                 445

Asp Ser Val Tyr Ala Val Gly Asn Val Ser Gln Leu Gly Asn Trp Ser
        450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Gln Val Gln Ala Ala Gly Ala Ser Thr Ser Gly
        515                 520                 525

Ser Phe
    530

<210> SEQ ID NO 3
<211> LENGTH: 530
<212> TYPE: PRT
<213> ORGANISM: Pseudomonas saccharophila

<400> SEQUENCE: 3

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Gly Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Pro Asp Pro Gly
130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270
```

```
Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
        515                 520                 525

Ser Phe
    530

<210> SEQ ID NO 4
<211> LENGTH: 530
<212> TYPE: PRT
<213> ORGANISM: Pseudomonas saccharophila

<400> SEQUENCE: 4

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
```

```
                100                 105                 110
Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
        515                 520                 525
```

```
Ser Phe
    530

<210> SEQ ID NO 5
<211> LENGTH: 530
<212> TYPE: PRT
<213> ORGANISM: Pseudomonas saccharophila

<400> SEQUENCE: 5

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Gly Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Pro Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
```

```
            355                 360                 365
Tyr Ser Gly Leu Val Ala Thr Val Ser Gly Ser Gln Gln Thr Leu Val
        370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
            420                 425                 430

Leu Val Asn Val Asn Phe Arg Cys Asp Asn Gly Val Thr Gln Met Gly
            435                 440                 445

Asp Ser Val Tyr Ala Val Gly Asn Val Ser Gln Leu Gly Asn Trp Ser
        450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
            515                 520                 525

Ser Phe
    530

<210> SEQ ID NO 6
<211> LENGTH: 530
<212> TYPE: PRT
<213> ORGANISM: Pseudomonas saccharophila

<400> SEQUENCE: 6

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190
```

-continued

```
Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
        260                 265                 270

Gly Leu Asn Gly Asn Pro Asp Pro Arg Trp Arg Glu Val Ala Val Thr
    275                 280                 285

Phe Val Asp Asn His Asp Thr Gly Tyr Ser Pro Gly Gln Asn Gly Gly
290                 295                 300

Gln His His Trp Ala Leu Gln Asp Pro Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
        340                 345                 350

Arg Thr Ala Gly Val Arg Ala Asp Ser Ala Ile Ser Phe His Ser Gly
    355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
        420                 425                 430

Leu Val Asn Val Asn Phe Arg Cys Asp Asn Gly Val Thr Gln Met Gly
    435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
        500                 505                 510

Gly Gly Asn Asn Gln Val Gln Ala Ala Gly Ala Ser Thr Ser Gly
    515                 520                 525

Ser Phe
    530

<210> SEQ ID NO 7
<211> LENGTH: 530
<212> TYPE: PRT
<213> ORGANISM: Pseudomonas saccharophila

<400> SEQUENCE: 7

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30
```

-continued

```
Asn Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
 50                  55                  60

Ser Trp Thr Asp Gly Gly Lys Ser Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
             100                 105                 110

Val Val Pro Asn His Met Asn Arg Gly Tyr Pro Asp Lys Glu Ile Asn
         115                 120                 125

Leu Pro Ala Gly Gln Gly Phe Trp Arg Asn Asp Cys Ala Asp Pro Gly
     130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                 165                 170                 175

Glu Leu Ala Asn Leu Arg Ser Gly Tyr Gly Ala Gly Gly Phe Arg Phe
             180                 185                 190

Asp Phe Val Arg Gly Tyr Ala Pro Glu Arg Val Asp Ser Trp Met Ser
         195                 200                 205

Asp Ser Ala Asp Ser Ser Phe Cys Val Gly Glu Leu Trp Lys Gly Pro
     210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                 245                 250                 255

Ala Leu Lys Glu Arg Met Gln Asn Gly Ser Val Ala Asp Trp Lys His
             260                 265                 270

Gly Leu Asn Gly Asn Pro Asp Pro Arg Trp Arg Glu Val Ala Val Thr
         275                 280                 285

Phe Val Asp Asn His Asp Thr Gly Tyr Ser Pro Gly Gln Asn Gly Gly
     290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                 325                 330                 335

Tyr Asp Trp Gly Tyr Gly Asp Phe Ile Arg Gln Leu Ile Gln Val Arg
             340                 345                 350

Arg Thr Ala Gly Val Arg Ala Asp Ser Ala Ile Ser Phe His Ser Gly
         355                 360                 365

Tyr Ser Gly Leu Val Ala Thr Val Ser Gly Ser Gln Gln Thr Leu Val
     370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                 405                 410                 415

Arg Ser Gly Ser Gly Asp Gly Gly Asn Asp Gly Gly Glu Gly Gly
             420                 425                 430

Leu Val Asn Val Asn Phe Arg Cys Asp Asn Gly Val Thr Gln Met Gly
         435                 440                 445
```

```
Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
                515                 520                 525

Ser Phe
    530

<210> SEQ ID NO 8
<211> LENGTH: 530
<212> TYPE: PRT
<213> ORGANISM: Pseudomonas saccharophila

<400> SEQUENCE: 8

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Gly Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Glu
145                 150                 155                 160

Ser Asp Leu Asn Thr Gly His Pro Gln Ile Tyr Gly Met Phe Arg Asp
                165                 170                 175

Glu Leu Ala Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Gly Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285
```

```
Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
                340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Pro
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
                420                 425                 430

Leu Val Asn Val Asn Phe Arg Cys Asp Asn Gly Val Thr Gln Met Gly
            435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
            500                 505                 510

Gly Gly Asn Asn Gln Val Gln Ala Ala Gly Ala Ser Thr Ser Gly
    515                 520                 525

Ser Phe
    530

<210> SEQ ID NO 9
<211> LENGTH: 551
<212> TYPE: PRT
<213> ORGANISM: Pseudomonas saccharophila

<400> SEQUENCE: 9

Met Ser His Ile Leu Arg Ala Ala Val Leu Ala Ala Val Leu Leu Pro
1               5                   10                  15

Phe Pro Ala Leu Ala Asp Gln Ala Gly Lys Ser Pro Ala Gly Val Arg
                20                  25                  30

Tyr His Gly Gly Asp Glu Ile Ile Leu Gln Gly Phe His Trp Asn Val
            35                  40                  45

Val Arg Glu Ala Pro Asn Asp Trp Tyr Asn Ile Leu Arg Gln Gln Ala
    50                  55                  60

Ser Thr Ile Ala Ala Asp Gly Phe Ser Ala Ile Trp Met Pro Val Pro
65                  70                  75                  80

Trp Arg Asp Phe Ser Ser Trp Thr Asp Gly Lys Ser Gly Gly Gly
                85                  90                  95

Glu Gly Tyr Phe Trp His Asp Phe Asn Lys Asn Gly Arg Tyr Gly Ser
            100                 105                 110

Asp Ala Gln Leu Arg Gln Ala Ala Gly Ala Leu Gly Gly Ala Gly Val
```

-continued

```
            115                 120                 125
Lys Val Leu Tyr Asp Val Pro Asn His Met Asn Arg Gly Tyr Pro
        130                 135                 140
Asp Lys Glu Ile Asn Leu Pro Ala Gly Gln Gly Phe Trp Arg Asn Asp
145                 150                 155                 160
Cys Ala Asp Pro Gly Asn Tyr Pro Asn Asp Cys Asp Asp Gly Asp Arg
                165                 170                 175
Phe Ile Gly Gly Glu Ser Asp Leu Asn Thr Gly His Pro Gln Ile Tyr
                180                 185                 190
Gly Met Phe Arg Asp Glu Leu Ala Asn Leu Arg Ser Gly Tyr Gly Ala
                195                 200                 205
Gly Gly Phe Arg Phe Asp Phe Val Arg Gly Tyr Ala Pro Glu Arg Val
        210                 215                 220
Asp Ser Trp Met Ser Asp Ser Ala Asp Ser Ser Phe Cys Val Gly Glu
225                 230                 235                 240
Leu Trp Lys Gly Pro Ser Glu Tyr Pro Ser Trp Asp Trp Arg Asn Thr
                245                 250                 255
Ala Ser Trp Gln Gln Ile Ile Lys Asp Trp Ser Asp Arg Ala Lys Cys
                260                 265                 270
Pro Val Phe Asp Phe Ala Leu Lys Glu Arg Met Gln Asn Gly Ser Val
        275                 280                 285
Ala Asp Trp Lys His Gly Leu Asn Gly Asn Pro Asp Pro Arg Trp Arg
        290                 295                 300
Glu Val Ala Val Thr Phe Val Asp Asn His Asp Thr Gly Tyr Ser Pro
305                 310                 315                 320
Gly Gln Asn Gly Gly Gln His His Trp Ala Leu Gln Asp Gly Leu Ile
                325                 330                 335
Arg Gln Ala Tyr Ala Tyr Ile Leu Thr Ser Pro Gly Thr Pro Val Val
                340                 345                 350
Tyr Trp Ser His Met Tyr Asp Trp Gly Tyr Gly Asp Phe Ile Arg Gln
                355                 360                 365
Leu Ile Gln Val Arg Arg Thr Ala Gly Val Arg Ala Asp Ser Ala Ile
        370                 375                 380
Ser Phe His Ser Gly Tyr Ser Gly Leu Val Ala Thr Val Ser Gly Ser
385                 390                 395                 400
Gln Gln Thr Leu Val Val Ala Leu Asn Ser Asp Leu Ala Asn Pro Gly
                405                 410                 415
Gln Val Ala Ser Gly Ser Phe Ser Glu Ala Val Asn Ala Ser Asn Gly
                420                 425                 430
Gln Val Arg Val Trp Arg Ser Gly Ser Gly Asp Gly Gly Gly Asn Asp
                435                 440                 445
Gly Gly Glu Gly Gly Leu Val Asn Val Asn Phe Arg Cys Asp Asn Gly
        450                 455                 460
Val Thr Gln Met Gly Asp Ser Val Tyr Ala Val Gly Asn Val Ser Gln
465                 470                 475                 480
Leu Gly Asn Trp Ser Pro Ala Ser Ala Val Arg Leu Thr Asp Thr Ser
                485                 490                 495
Ser Tyr Pro Thr Trp Lys Gly Ser Ile Ala Leu Pro Asp Gly Gln Asn
                500                 505                 510
Val Glu Trp Lys Cys Leu Ile Arg Asn Glu Ala Asp Ala Thr Leu Val
        515                 520                 525
Arg Gln Trp Gln Ser Gly Gly Asn Asn Gln Val Gln Ala Ala Ala Gly
        530                 535                 540
```

Ala Ser Thr Ser Gly Ser Phe
545             550

<210> SEQ ID NO 10
<211> LENGTH: 3050
<212> TYPE: DNA
<213> ORGANISM: Pseudomonas saccharophila

<400> SEQUENCE: 10

| | | | | |
|---|---|---|---|---|
| gatcggcgta | ggtttcgcat | tcgttgccca | ggcgatattt | cgccggtgcg ccagcagcct | 60 |
| ggaagcaggc | ctggtcgccg | ccgccggccg | tggcgccgac | gcccgaacgc agatagccgt | 120 |
| ggaaatcgac | cgccagggcc | gggccgccga | ccagcagggc | ggcaagcagg caggcgggtt | 180 |
| ttaggacgaa | caggggtgc | gcggtgtgct | tcatgacgag | gtccttgttt ttcttgttaa | 240 |
| tgccgaatcg | atcacgcctt | cgctgcgtgt | cgcagggcgc | agctcggtgg cgaaagcctc | 300 |
| ggggatggct | ccgctggcgg | catcctcccg | accagagatt | cgctggcgc agctcgaggg | 360 |
| cgtaatcagg | atgagtgcgg | cgtaatccct | ggggtggggc | tacgcccggc agggcgcaga | 420 |
| tgattgccag | gggccttcgg | cctggccact | acgccgcctg | caactgggcg ggggaggttg | 480 |
| gtggtcgggg | cgtgcagggg | cagcctgcgg | gtgccggtcg | aagacccggc cggcgttcat | 540 |
| cctcgtccgg | cggccttgcc | gtaggatacc | cgaacaagca | caagaaccgg agtattgcga | 600 |
| tgagccacat | cctgcgtgcc | gccgtattgg | cggcggtcct | gctgccgttt cccgcactgg | 660 |
| ccgatcaggc | cggcaagagc | ccggccgggg | tgcgctacca | cggcggcgac gaaatcatcc | 720 |
| tccagggctt | ccactggaac | gtcgtccgcg | aagcgcccaa | cgactggtac aacatcctcc | 780 |
| gccaacaggc | ctcgacgatc | gcggccgacg | gcttctcggc | aatctggatg ccggtgccct | 840 |
| ggcgtgactt | ctccagctgg | accgacggcg | gcaagtccgg | cggcggcgaa ggctacttct | 900 |
| ggcacgactt | caacaagaac | ggccgctacg | gcagcgacgc | ccagctgcgc caggccgccg | 960 |
| gcgcactcgg | tggcgccggg | gtgaaggtgc | tctacgatgt | ggtgcccaat cacatgaacc | 1020 |
| gcggctaccc | ggacaaggag | atcaacctgc | cggccggcca | gggcttctgg cgcaacgact | 1080 |
| gcgccgaccc | gggcaactac | cccaacgact | gcgacgacgg | tgaccgcttc atcggcggcg | 1140 |
| agtcggacct | gaacaccggc | catccgcaga | tttacggcat | gttcgcgac gagcttgcca | 1200 |
| acctgcgcag | cggctacggc | gccggcggct | tccgcttcga | cttcgttcgc ggctatgcgc | 1260 |
| ccgagcgggt | cgacgctgg | atgagcgaca | gcgccgacag | cagcttctgc gttggcgagc | 1320 |
| tgtggaaagg | cccttctgaa | tatccgagct | gggactggcg | caacacggcg agctggcagc | 1380 |
| agatcatcaa | ggactggtcc | gaccgggcca | agtgcccggt | gttcgacttc gctctcaagg | 1440 |
| agcgcatgca | gaacggctcg | gtcgccgact | ggaagcatgg | cctcaatggc aaccccgacc | 1500 |
| cgcgctggcg | cgaggtggcg | gtgaccttcg | tcgacaacca | cgacaccggc tattcgcccg | 1560 |
| ggcagaacgg | cggccagcac | cactgggcgc | tgcaggacgg | gctgatccgc caggcctacg | 1620 |
| cctacatcct | caccagcccg | ggcacgccgg | tggtgtactg | gtcgcacatg tacgactggg | 1680 |
| gctacgccga | cttcatccgc | cagctgatcc | aggtgcggcg | caccgccggc gtgcgcgccg | 1740 |
| attcggcgat | cagcttccat | agcggctaca | gcggtctggt | cgctaccgtc agcggcagcc | 1800 |
| agcagaccct | ggtggtggcg | ctcaactccg | atctggccaa | ccccgccag gttgccagcg | 1860 |
| gcagcttcag | cgaggcggtc | aacgccagca | acggccaggt | gcgcgtctgg cgcagcggta | 1920 |
| gcggcgatgg | cggcgggaat | gacgcggcg | agggtggctt | ggtcaatgtg aactttcgct | 1980 |
| gcgacaacgg | cgtgacgcag | atgggcgaca | gcgtctacgc | ggtgggcaac gtcagccagc | 2040 |

-continued

```
tcggcaactg gagcccggcc tccgcggtac ggctgaccga caccagcagc tatccgacct    2100
ggaagggcag catcgccctg cctgacggtc agaacgtgga atggaagtgc ctgatccgca    2160
acgaggcgga cgcgacgctg gtgcgtcagt ggcaatcggg cggcaacaac caggtccagg    2220
ccgccgccgg cgcgagcacc agcggctcgt tctgacgaca tgcccgcccg gcctcggcta    2280
cgcctacgcc gggcggctcc tcccgaccca gggtgggcag ggaggaggcc ggcgacgggc    2340
cgggccgccg atgctggcac gacaaccata aaagccttcg cgctgcgctg tcgtatcagg    2400
agctgttcat gttggcccag acccgctcga ccccttttccg gcttggcttc ctggcccggc    2460
tgtacctgct gatcgccgca ctggtggcct tgctgatgct ggtagccggc accagcctgg    2520
ttgccatcgg ccgcctgcaa ggcaatgccg agcaaatctc gtcgaccgcg tcgcgtctgc    2580
tggtcagcga gagcttcttc ggtacgttgc agagcctgac gcagaacctg tccgacgccc    2640
tggccgagga ccggcctgac cagctcgacg gctatgtcgg ccggcatcgc acgctgcagg    2700
accaggccct cgagctgttc gcccagctgg agcgggtgac gccggcacat gccgagacca    2760
agcaagcctg gcggcgctgt tgccggagct cgaccgccgc agcctggcgc tgatcgatgc    2820
gcacgcgacc tgctcgcgcg tggggcgcaa cgccgtcgcc tgcgcgatct gcagctgcag    2880
ttctcgcggc tcaagcagga cctgctgcag gcgcagttcg tgacgggcga cgagctggtc    2940
gcctattcca tcaagcagtt catcatcccg ctcgagcagg tcgagcgctg ctgttcgatg    3000
ccatcggcgt gtcttcgatc aaggcactcg atgaagcggg tgcgcagatc                3050
```

<210> SEQ ID NO 11
<211> LENGTH: 527
<212> TYPE: PRT
<213> ORGANISM: Pseudomonas stutzeri

<400> SEQUENCE: 11

```
Asp Gln Ala Gly Lys Ser Pro Asn Ala Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ala Thr Ile Ala Ala
         35                  40                  45

Asp Gly Phe Ser Ala Ile Trp Met Pro Val Pro Trp Arg Asp Phe Ser
     50                  55                  60

Ser Trp Ser Asp Gly Ser Lys Ser Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190
```

-continued

```
Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Gly Pro
210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525
```

<210> SEQ ID NO 12
<211> LENGTH: 527
<212> TYPE: PRT
<213> ORGANISM: Pseudomonas stutzeri

<400> SEQUENCE: 12

```
Asp Gln Ala Gly Lys Ser Pro Asn Ala Val Arg Tyr His Gly Gly Asp
 1               5                  10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ala Thr Ile Ala Ala
        35                  40                  45
```

-continued

```
Asp Gly Phe Ser Ala Ile Trp Met Pro Val Pro Trp Arg Asp Phe Ser
         50                  55                  60

Ser Trp Ser Asp Pro Ser Lys Ser Gly Gly Glu Gly Tyr Phe Trp
 65                  70                  75                  80

His Asp Phe Asn Lys Asn Gly Arg Tyr Gly Ser Asp Ala Gln Leu Arg
                     85                  90                  95

Gln Ala Ala Ser Ala Leu Gly Gly Ala Gly Val Lys Val Leu Tyr Asp
                100                 105                 110

Val Val Pro Asn His Met Asn Arg Gly Tyr Pro Asp Lys Glu Ile Asn
            115                 120                 125

Leu Pro Ala Gly Gln Gly Phe Trp Arg Asn Asp Cys Ala Asp Pro Gly
        130                 135                 140

Asn Tyr Pro Asn Asp Cys Asp Gly Asp Arg Phe Ile Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
                180                 185                 190

Asp Phe Val Arg Gly Tyr Ala Pro Glu Arg Val Asn Ser Trp Met Thr
            195                 200                 205

Asp Ser Ala Asp Asn Ser Phe Cys Val Gly Glu Leu Trp Lys Gly Pro
        210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
                260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
        290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
450                 455                 460
```

```
Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
            485                 490                 495

Asn Glu Ala Asn Ala Thr Gln Val Arg Gln Trp Gln Gly Gly Ala Asn
        500                 505                 510

Asn Ser Leu Thr Pro Ser Glu Gly Ala Thr Thr Val Gly Arg Leu
    515                 520                 525

<210> SEQ ID NO 13
<211> LENGTH: 527
<212> TYPE: PRT
<213> ORGANISM: Pseudomonas stutzeri

<400> SEQUENCE: 13

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
                20                  25                  30

Asn Asp Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Gly Ser Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Pro Asp Pro Gly
130                 135                 140

Asn Tyr Pro Asn Asp Cys Asp Asp Gly Asp Arg Phe Ile Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Gly Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320
```

```
Tyr Ile Leu Thr Ser Pro Gly Thr Pro Val Val Tyr Trp Ser His Met
            325                 330                 335

Tyr Asp Trp Gly Tyr Gly Asp Phe Ile Arg Gln Leu Ile Gln Val Arg
        340                 345                 350

Arg Ala Ala Gly Val Arg Ala Asp Ser Ala Ile Ser Phe His Ser Gly
    355                 360                 365

Tyr Ser Gly Leu Val Ala Thr Val Ser Gly Ser Gln Gln Thr Leu Val
370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525

<210> SEQ ID NO 14
<211> LENGTH: 527
<212> TYPE: PRT
<213> ORGANISM: Pseudomonas stutzeri

<400> SEQUENCE: 14

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Gly Ser Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Asp
145                 150                 155                 160

Ala Asp Leu Asn Thr Gly His Pro Gln Val Tyr Gly Met Phe Arg Asp
```

```
            165                 170                 175
Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
            195                 200                 205

Asp Ser Ala Asp Asn Ser Phe Cys Val Gly Glu Leu Trp Lys Ala Pro
            210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
            245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
            290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
            325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
            370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
            405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
            435                 440                 445

Tyr Ala Val Gly Asn Val Ser Gln Leu Gly Asn Trp Ser Pro Ala Ala
            450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
            485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
            515                 520                 525

<210> SEQ ID NO 15
<211> LENGTH: 527
<212> TYPE: PRT
<213> ORGANISM: Pseudomonas stutzeri

<400> SEQUENCE: 15

Asp Gln Ala Gly Lys Ser Pro Asn Ala Val Arg Tyr His Gly Gly Asp
1               5                   10                  15
```

-continued

```
Glu Ile Ile Leu Gln Gly Phe His Trp Asn Val Val Arg Glu Ala Pro
             20                      25                  30

Asn Asp Trp Tyr Asn Ile Leu Arg Gln Gln Ala Ala Thr Ile Ala Ala
             35                  40              45

Asp Gly Phe Ser Ala Ile Trp Met Pro Val Pro Trp Arg Asp Phe Ser
         50                  55                  60

Ser Trp Ser Asp Gly Ser Lys Ser Gly Gly Glu Gly Tyr Phe Trp
65                      70                  75                  80

His Asp Phe Asn Lys Asn Gly Arg Tyr Gly Ser Asp Ala Gln Leu Arg
                 85                  90                  95

Gln Ala Ala Ser Ala Leu Gly Ala Gly Val Lys Val Leu Tyr Asp
                 100                 105                 110

Val Val Pro Asn His Met Asn Arg Gly Tyr Pro Asp Lys Glu Ile Asn
             115                 120                 125

Leu Pro Ala Gly Gln Gly Phe Trp Arg Asn Asp Cys Ala Asp Pro Gly
    130                 135                 140

Asn Tyr Pro Asn Asp Cys Asp Asp Gly Asp Arg Phe Ile Gly Gly Asp
145                 150                 155                 160

Ala Asp Leu Asn Thr Gly His Pro Gln Val Tyr Gly Met Phe Arg Asp
                 165                 170                 175

Glu Phe Thr Asn Leu Arg Ser Gln Tyr Gly Ala Gly Gly Phe Arg Phe
             180                 185                 190

Asp Phe Val Arg Gly Tyr Ala Pro Glu Arg Val Asn Ser Trp Met Thr
             195                 200                 205

Asp Ser Ala Asp Asn Ser Phe Cys Val Gly Glu Leu Trp Lys Gly Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                 245                 250                 255

Ala Leu Lys Glu Arg Met Gln Asn Gly Ser Ile Pro Asp Trp Lys His
             260                 265                 270

Gly Leu Asn Gly Asn Pro Asp Pro Arg Trp Arg Glu Val Ala Val Thr
         275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                 325                 330                 335

Tyr Asp Trp Gly Tyr Gly Asp Phe Ile Arg Gln Leu Ile Gln Val Arg
             340                 345                 350

Arg Ala Ala Gly Val Arg Ala Asp Ser Ala Ile Ser Phe His Ser Gly
             355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                 405                 410                 415

Arg Ser Gly Thr Gly Ser Gly Gly Glu Pro Gly Ala Leu Val Ser
             420                 425                 430

Val Ser Phe Arg Cys Asp Asn Gly Ala Thr Gln Met Gly Asp Ser Val
```

-continued

```
                435                 440                 445
Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Ala Asn
                500                 505                 510

Asn Ser Leu Thr Pro Ser Glu Gly Ala Thr Thr Val Gly Arg Leu
        515                 520                 525

<210> SEQ ID NO 16
<211> LENGTH: 527
<212> TYPE: PRT
<213> ORGANISM: Pseudomonas stutzeri

<400> SEQUENCE: 16

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
                20                  25                  30

Asn Asp Trp Tyr Asn Ile Leu Arg Gln Gln Ala Ala Thr Ile Ala Ala
            35                  40                  45

Asp Gly Phe Ser Ala Ile Trp Met Pro Val Pro Trp Arg Asp Phe Ser
    50                  55                  60

Ser Trp Ser Asp Gly Ser Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Gly Asp Arg Phe Ile Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Gly Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285
```

```
Phe Val Asp Asn His Asp Thr Gly Tyr Ser Pro Gly Gln Asn Gly Gly
    290                 295                 300

Gln His His Trp Ala Leu Gln Asp Pro Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
        515                 520                 525

<210> SEQ ID NO 17
<211> LENGTH: 527
<212> TYPE: PRT
<213> ORGANISM: Pseudomonas stutzeri

<400> SEQUENCE: 17

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Gly Ser Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140
```

```
Asn Tyr Pro Asn Asp Cys Asp Asp Gly Asp Arg Phe Ile Gly Gly Asp
145                 150                 155                 160

Ala Asp Leu Asn Thr Gly His Pro Gln Val Tyr Gly Met Phe Arg Asp
            165                 170                 175

Glu Phe Thr Asn Leu Arg Ser Gln Tyr Gly Ala Gly Phe Arg Phe
            180                 185                 190

Asp Phe Val Arg Gly Tyr Ala Pro Glu Arg Val Asn Ser Trp Met Thr
            195                 200                 205

Asp Ser Ala Asp Asn Ser Phe Cys Val Gly Glu Leu Trp Lys Gly Pro
210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
275                 280                 285

Phe Val Asp Asn His Asp Thr Gly Tyr Ser Pro Gly Gln Asn Gly Gly
290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
370                 375                 380

Val Ala Leu Asn Ser Asp Leu Gly Asn Pro Gly Gln Val Ala Pro Gly
385                 390                 395                 400

Ser Phe Ser Glu Ala Val Asn Ala Ser Asn Gly Gln Val Arg Val Trp
            405                 410                 415

Arg Ser Gly Thr Gly Ser Gly Gly Gly Glu Pro Gly Ala Leu Val Ser
            420                 425                 430

Val Ser Phe Arg Cys Asp Asn Gly Ala Thr Gln Met Gly Asp Ser Val
            435                 440                 445

Tyr Ala Val Gly Asn Val Ser Gln Leu Gly Asn Trp Ser Pro Ala Ala
450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
            500                 505                 510

Asn Ser Leu Thr Pro Ser Glu Gly Ala Thr Thr Val Gly Arg Leu
            515                 520                 525

<210> SEQ ID NO 18
<211> LENGTH: 527
<212> TYPE: PRT
<213> ORGANISM: Pseudomonas stutzeri
```

<400> SEQUENCE: 18

```
Asp Gln Ala Gly Lys Ser Pro Asn Ala Val Arg Tyr His Gly Gly Asp
 1               5                  10                  15
Glu Ile Ile Leu Gln Gly Phe His Trp Asn Val Val Arg Glu Ala Pro
             20                  25                  30
Asn Asp Trp Tyr Asn Ile Leu Arg Gln Gln Ala Ala Thr Ile Ala Ala
         35                  40                  45
Asp Gly Phe Ser Ala Ile Trp Met Pro Val Pro Trp Arg Asp Phe Ser
 50                  55                  60
Ser Trp Ser Asp Gly Ser Lys Ser Gly Gly Glu Gly Tyr Phe Trp
 65                  70                  75                  80
His Asp Phe Asn Lys Asn Gly Arg Tyr Gly Ser Asp Ala Gln Leu Arg
                 85                  90                  95
Gln Ala Ala Ser Ala Leu Gly Gly Ala Gly Val Lys Val Leu Tyr Asp
            100                 105                 110
Val Val Pro Asn His Met Asn Arg Gly Tyr Pro Asp Lys Glu Ile Asn
            115                 120                 125
Leu Pro Ala Gly Gln Gly Phe Trp Arg Asn Asp Cys Ala Asp Pro Gly
        130                 135                 140
Asn Tyr Pro Asn Asp Cys Asp Asp Gly Asp Arg Phe Ile Gly Gly Asp
145                 150                 155                 160
Ala Asp Leu Asn Thr Gly His Pro Gln Val Tyr Gly Met Phe Arg Asp
                165                 170                 175
Glu Phe Thr Asn Leu Arg Ser Gln Tyr Gly Ala Gly Gly Phe Arg Phe
            180                 185                 190
Asp Phe Val Arg Gly Tyr Ala Pro Glu Arg Val Asn Ser Trp Met Thr
        195                 200                 205
Asp Ser Ala Asp Asn Ser Phe Cys Val Gly Glu Leu Trp Lys Gly Pro
210                 215                 220
Ser Glu Tyr Pro Asn Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Ile Ala Asp Trp Lys His
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Gly Gly
        290                 295                 300
Gln His His Trp Ala Leu Gln Asp Gly Leu Ile Arg Gln Ala Tyr Ala
305                 310                 315                 320
Tyr Ile Leu Thr Ser Pro Gly Thr Pro Val Val Tyr Trp Ser His Met
                325                 330                 335
Tyr Asp Trp Gly Tyr Gly Asp Phe Ile Arg Gln Leu Ile Gln Val Arg
            340                 345                 350
Arg Ala Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
    370                 375                 380
Val Ala Leu Asn Ser Asp Leu Gly Asn Pro Gly Gln Val Ala Ser Pro
385                 390                 395                 400
Ser Phe Ser Glu Ala Val Asn Ala Ser Asn Gly Gln Val Arg Val Trp
                405                 410                 415
```

-continued

```
Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
            435                 440                 445

Tyr Ala Val Gly Asn Val Ser Gln Leu Gly Asn Trp Ser Pro Ala Ala
            450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Trp Lys Cys Leu Ile Arg
                485                 490                 495

Asn Glu Ala Asn Ala Thr Gln Val Arg Gln Trp Gln Gly Ala Asn
            500                 505                 510

Asn Ser Leu Thr Pro Ser Glu Gly Ala Thr Thr Val Gly Arg Leu
            515                 520                 525
```

<210> SEQ ID NO 19
<211> LENGTH: 548
<212> TYPE: PRT
<213> ORGANISM: Pseudomonas stutzeri

<400> SEQUENCE: 19

```
Met Ser His Ile Leu Arg Ala Val Leu Ala Ala Met Leu Leu Pro
  1               5                  10                  15

Leu Pro Ser Met Ala Asp Gln Ala Gly Lys Ser Pro Asn Ala Val Arg
                20                  25                  30

Tyr His Gly Gly Asp Glu Ile Leu Gln Gly Phe His Trp Asn Val
            35                  40                  45

Val Arg Glu Ala Pro Asn Asp Trp Tyr Asn Ile Leu Arg Gln Gln Ala
        50                  55                  60

Ala Thr Ile Ala Ala Asp Gly Phe Ser Ala Ile Trp Met Pro Val Pro
65                  70                  75                  80

Trp Arg Asp Phe Ser Ser Trp Ser Asp Gly Ser Lys Ser Gly Gly Gly
                85                  90                  95

Glu Gly Tyr Phe Trp His Asp Phe Asn Lys Asn Gly Arg Tyr Gly Ser
                100                 105                 110

Asp Ala Gln Leu Arg Gln Ala Ser Ala Leu Gly Gly Ala Gly Val
            115                 120                 125

Lys Val Leu Tyr Asp Val Val Pro Asn His Met Asn Arg Gly Tyr Pro
130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Asp Gly Asp Arg
                165                 170                 175

Phe Ile Gly Gly Asp Ala Asp Leu Asn Thr Gly His Pro Gln Val Tyr
            180                 185                 190

Gly Met Phe Arg Asp Glu Phe Thr Asn Leu Arg Ser Gln Tyr Gly Ala
            195                 200                 205

Gly Gly Phe Arg Phe Asp Phe Val Arg Gly Tyr Ala Pro Glu Arg Val
            210                 215                 220

Asn Ser Trp Met Thr Asp Ser Ala Asp Asn Ser Phe Cys Val Gly Glu
225                 230                 235                 240

Leu Trp Lys Gly Pro Ser Glu Tyr Pro Asn Trp Asp Trp Arg Asn Thr
                245                 250                 255

Ala Ser Trp Gln Gln Ile Ile Lys Asp Trp Ser Asp Arg Ala Lys Cys
```

```
                260                  265                  270
Pro Val Phe Asp Phe Ala Leu Lys Glu Arg Met Gln Asn Gly Ser Ile
        275                  280                  285
Ala Asp Trp Lys His Gly Leu Asn Gly Asn Pro Asp Pro Arg Trp Arg
    290                  295                  300
Glu Val Ala Val Thr Phe Val Asp Asn His Asp Thr Gly Tyr Ser Pro
305                  310                  315                  320
Gly Gln Asn Gly Gly Gln His His Trp Ala Leu Gln Asp Gly Leu Ile
                325                  330                  335
Arg Gln Ala Tyr Ala Tyr Ile Leu Thr Ser Pro Gly Thr Pro Val Val
            340                  345                  350
Tyr Trp Ser His Met Tyr Asp Trp Gly Tyr Gly Asp Phe Ile Arg Gln
                355                  360                  365
Leu Ile Gln Val Arg Arg Ala Ala Gly Val Arg Ala Asp Ser Ala Ile
    370                  375                  380
Ser Phe His Ser Gly Tyr Ser Gly Leu Val Ala Thr Val Ser Gly Ser
385                  390                  395                  400
Gln Gln Thr Leu Val Val Ala Leu Asn Ser Asp Leu Gly Asn Pro Gly
                405                  410                  415
Gln Val Ala Ser Gly Ser Phe Ser Glu Ala Val Asn Ala Ser Asn Gly
            420                  425                  430
Gln Val Arg Val Trp Arg Ser Gly Thr Gly Ser Gly Gly Glu Pro
    435                  440                  445
Gly Ala Leu Val Ser Val Ser Phe Arg Cys Asp Asn Gly Ala Thr Gln
    450                  455                  460
Met Gly Asp Ser Val Tyr Ala Val Gly Asn Val Ser Gln Leu Gly Asn
465                  470                  475                  480
Trp Ser Pro Ala Ala Ala Leu Arg Leu Thr Asp Thr Ser Gly Tyr Pro
                485                  490                  495
Thr Trp Lys Gly Ser Ile Ala Leu Pro Ala Gly Gln Asn Glu Glu Trp
            500                  505                  510
Lys Cys Leu Ile Arg Asn Glu Ala Asn Ala Thr Gln Val Arg Gln Trp
    515                  520                  525
Gln Gly Gly Ala Asn Asn Ser Leu Thr Pro Ser Glu Gly Ala Thr Thr
    530                  535                  540
Val Gly Arg Leu
545

<210> SEQ ID NO 20
<211> LENGTH: 2082
<212> TYPE: DNA
<213> ORGANISM: Pseudomonas stutzeri

<400> SEQUENCE: 20
gatcggcctt tacggaaagt gatagagctt ctcttccggc aaactttgtt ccccagtgac     60
agagggttag tatcggatcg cttcctcttt gggtttggta gatcaggagc gccgagagca    120
ggatgaaatc ctgcgccag aaggtcgcgc cgaagatgtg gaactgctgc tggccgagat    180
ccggccggcg ttcatcctcg tccggcggcc ttgccgccag ctacccgaac aagcacaaga    240
accggagtat tgcgatgagc acatcctgc gagccgccgt attggcggcg atgctgttgc    300
cgttgccgtc catggccgat caggccggca agagcccaa cgctgtgcgc taccacggcg    360
gcgacgaaat cattctccag ggcttttcact ggaacgtcgt ccgcgaagcg cccaacgact    420
ggtacaacat cctgcgccag caggccgcga ccatcgccgc cgacggcttc tcggcgatct    480
```

-continued

```
ggatgccggt gccctggcgc gacttctcca gctggagcga cggcagcaag tccggcggcg      540
gtgaaggcta cttctggcac gacttcaaca agaacggccg ctatggcagt gacgcccagc      600
tgcgtcaggc cgccagcgcg ctcggtggcg ccggcgtgaa agtgctttac gacgtggtgc      660
ccaaccacat gaaccgtggc tatccggaca aggagatcaa cctcccggcc ggccagggct      720
tctggcgcaa cgactgcgcc gacccgggca actaccccaa tgattgcgac gacggcgacc      780
gcttcatcgg cggcgatgcg gacctcaaca ccggccaccc gcaggtctac ggcatgttcc      840
gcgatgaatt caccaacctg cgcagtcagt acggtgccgg cggcttccgc ttcgactttg      900
ttcggggcta tgcgccggag cgggtcaaca gctggatgac cgatagcgcc gacaacagct      960
tctgcgtcgg cgaactgtgg aaaggcccct ctgagtaccc gaactgggac tggcgcaaca     1020
ccgccagctg gcagcagatc atcaaggact ggtccgaccg ggccaagtgc ccggtgttcg     1080
acttcgccct caaggaacgc atgcagaacg ctcgatcgcc gactggaagc acgcctgaac     1140
ggcaatcccg acccgcgtgg cgcgaggtgg cggtgacctt cgtcgacaac cacgacaccg     1200
gctactcgcc cgggcagaac ggtgggcagc accactgggc tctgcaggac gggctgatcc     1260
gccaggccta cgcctacatc ctcaccagcc ccggtacgcc ggtggtgtac tggtcgcaca     1320
tgtacgactg gggttacggc gacttcatcc gtcagctgat ccaggtgcgt cgcgccgccg     1380
gcgtgcgcgc cgattcggcg atcagcttcc acagcggcta cagcggtctg gtcgccaccg     1440
tcagcggcag ccagcagacc ctggtggtgg cgctcaactc cgacctgggc aatcccggcc     1500
aggtggccag cggcagcttc agcgaggcgg tcaacgccag caacgccagt gtgcgcgtgt     1560
ggcgtagcgg cacgggcagc ggtggcggtg aacccggcgc tctggtcagt gtgagtttcc     1620
gctgcgacaa cggcgcgacg cagatgggcg acagcgtcta cgcggtcggc aacgtcagcc     1680
agctcggtaa ctggagcccg gccgcggcgt tgcgcctgac cgacaccagc ggctacccga     1740
cctggaaggg cagcattgcc ttgcctgccg gccagaacga ggaatggaaa tgcctgatcc     1800
gcaacgaggc caacgccacc caggtgcggc aatggcaggg cggggcaaac aacagcctga     1860
cgccgagcga gggcgccacc accgtcggcc ggctctagcc cgggcggcaa ctcggccgtc     1920
tcgcggatgt gaggcggctg gtctcggcgg cggtatcgtt gcgctggggg cggggccgcc     1980
gttcacgcgc cctgctatcg ctagttttcg gcgctccgcg catcggccag ttgccagcga     2040
atcgcctgcg cttcggcctg gtgcaggtcg tcgagcagcg ct                        2082
```

<210> SEQ ID NO 21
<211> LENGTH: 21
<212> TYPE: PRT
<213> ORGANISM: Pseudomonas saccharophila

<400> SEQUENCE: 21

Met Ser His Ile Leu Arg Ala Ala Val Leu Ala Ala Val Leu Leu Pro
 1               5                  10                  15

Phe Pro Ala Leu Ala
            20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
atgacgaggt ccttgttttt c                                              21
```

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
cgctagtcgt ccatgtcg                                                  18
```

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
gccatggatc aggccggcaa gagcccg                                        27
```

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
tggatcctca gaacgagccg ctggt                                          25
```

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gaattcagcc gccgtcattc ccgcc                                          25
```

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
agatttacgg catgtttcgc                                                20
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

-continued tagccgctat ggaagctgat       20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgaccttcgt cgacaaccac       20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatagctgct ggtgacggtc       20

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agctggaccg acccgggcaa gtccggc       27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gccggcgcac tccctggcgc cggggtg       27

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cacatgaacc gcccgtaccc ggacaag       27

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caacctgccg gccccgcagg gcttctgg       28

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgcaacgact gcccggatcc gggcaac                                        27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atcggcggcg agccagatct gaacacc                                        27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gttcgcggct atccgcccga gcgggtc                                        27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gacagcgccg acccaagctt ctgcgtt                                        27

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gagctgtgga aagccccttc tgaatatc                                       28

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aacggctcgg tcccggactg gaagcat                                        27

```
<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcgctgcagg acccgctgat ccgccag                                            27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gactggggct acccggactt catccgc                                            27

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcgataagct tccatccggg ctacagc                                            27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggccaggttg ccccgggaag cttcagc                                            27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caggttgcca gcccgagctt cagcgag                                            27
```